United States Patent
Zhang et al.

(10) Patent No.: US 11,534,242 B2
(45) Date of Patent: Dec. 27, 2022

(54) SURGICAL SYSTEMS AND METHODS FOR IDENTIFYING TOOLS GUIDED BY SURGICAL ROBOTS

(71) Applicant: MAKO Surgical Corp., Ft. Lauderdale, FL (US)

(72) Inventors: Zenan Zhang, Weston, FL (US); Kevin Bechtold, Davie, FL (US); Carl Gayle, Plantation, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 855 days.

(21) Appl. No.: 16/279,464

(22) Filed: Feb. 19, 2019

(65) Prior Publication Data

US 2019/0254756 A1 Aug. 22, 2019

Related U.S. Application Data

(60) Provisional application No. 62/631,995, filed on Feb. 19, 2018.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/30* (2016.02); *A61B 90/361* (2016.02);
(Continued)

(58) Field of Classification Search
CPC ......... A61B 34/20; A61B 90/90; A61B 34/10; A61B 34/30; A61B 90/361;
(Continued)

(56) References Cited

U.S. PATENT DOCUMENTS

| 7,725,162 B2 | 5/2010 | Malackowski et al. |
| 7,813,784 B2 | 10/2010 | Marquart et al. |

(Continued)

FOREIGN PATENT DOCUMENTS

| WO | 2007056743 A1 | 5/2007 |
| WO | 2017205351 A1 | 11/2017 |

OTHER PUBLICATIONS

International Search Report for Application No. PCT/US2019/018500 dated May 31, 2019, 5 pages.
(Continued)

*Primary Examiner* — Basil T. Jos
(74) *Attorney, Agent, or Firm* — Howard & Howard Attorneys PLLC

(57) ABSTRACT

A surgical system for assisting a user in performing a surgical procedure at a surgical site, comprising a tool having a checkpoint, a pointer having a tip, and a localizer to determine a position of the pointer within a field of view. A memory comprises identification data associated with a plurality of tools. A controller is configured to prompt the user to position the tip of at the checkpoint, to receive position data from the localizer associated with the pointer within the field of view, to compare position data associated with the pointer against the identification data of the memory to determine an identity of the tool, and to present the user with the identity of the tool.

27 Claims, 26 Drawing Sheets

(51) Int. Cl.
  *A61B 34/30* (2016.01)
  *A61B 90/00* (2016.01)
  *A61B 90/90* (2016.01)
  *A61F 2/34* (2006.01)
  *A61B 34/00* (2016.01)
  *A61F 2/46* (2006.01)

(52) U.S. Cl.
  CPC ................ *A61B 90/90* (2016.02); *A61F 2/34* (2013.01); *A61B 2034/207* (2016.02); *A61B 2034/2051* (2016.02); *A61B 2034/2055* (2016.02); *A61B 2034/2057* (2016.02); *A61B 2034/2063* (2016.02); *A61B 2034/2068* (2016.02); *A61B 2034/2074* (2016.02); *A61B 2034/252* (2016.02); *A61B 2034/256* (2016.02); *A61F 2/4607* (2013.01); *A61F 2002/4632* (2013.01)

(58) Field of Classification Search
  CPC ........ A61B 2034/256; A61B 2034/252; A61B 2034/207; A61B 2034/2055; A61B 2034/2051; A61B 2034/2057; A61B 2034/2063; A61B 2034/2068; A61B 2034/2074; A61F 2/34; A61F 2/4607; A61F 2002/4632
  See application file for complete search history.

(56) References Cited

U.S. PATENT DOCUMENTS

| | | |
|---|---|---|
| 8,010,180 B2 | 8/2011 | Quaid et al. |
| 8,753,346 B2 | 6/2014 | Suarez et al. |
| 8,979,859 B2 | 3/2015 | Leparmentier et al. |
| 9,008,757 B2 | 4/2015 | Wu |
| 9,119,655 B2 | 9/2015 | Bowling et al. |
| 2004/0054489 A1 | 3/2004 | Moctezuma De La Barrera et al. |
| 2016/0022374 A1 | 1/2016 | Haider |
| 2017/0000583 A1 | 1/2017 | Lechner et al. |

OTHER PUBLICATIONS

Stryker, "Mako THA Application User Guide", PN 212026 Rev. 00, Sep. 2015, 141 pages.

IM3, 78B

| Case Planning | Pre-Op Check | Femoral Prep | Acetabular Prep | Final Results |

Options | Screen

Cup Size: 56mm
Reamer Size: 56mm

Reamer Size: 56mm ▶

Reamer: Straight ▶
1st Option
2nd Option 45°
2nd Option 90°
2nd Option 135°

Place the distal tip of the pointer in the divot on the reamer handle.

Cup Reaming
Back | Next

REQUIRED SURGEON ACKNOWLEDGEMENT:
You are about to resect bone in accordance with your preoperative surgical plan. By continuing, you acknowledge sole responsibility for the advisability and validity of the plan.

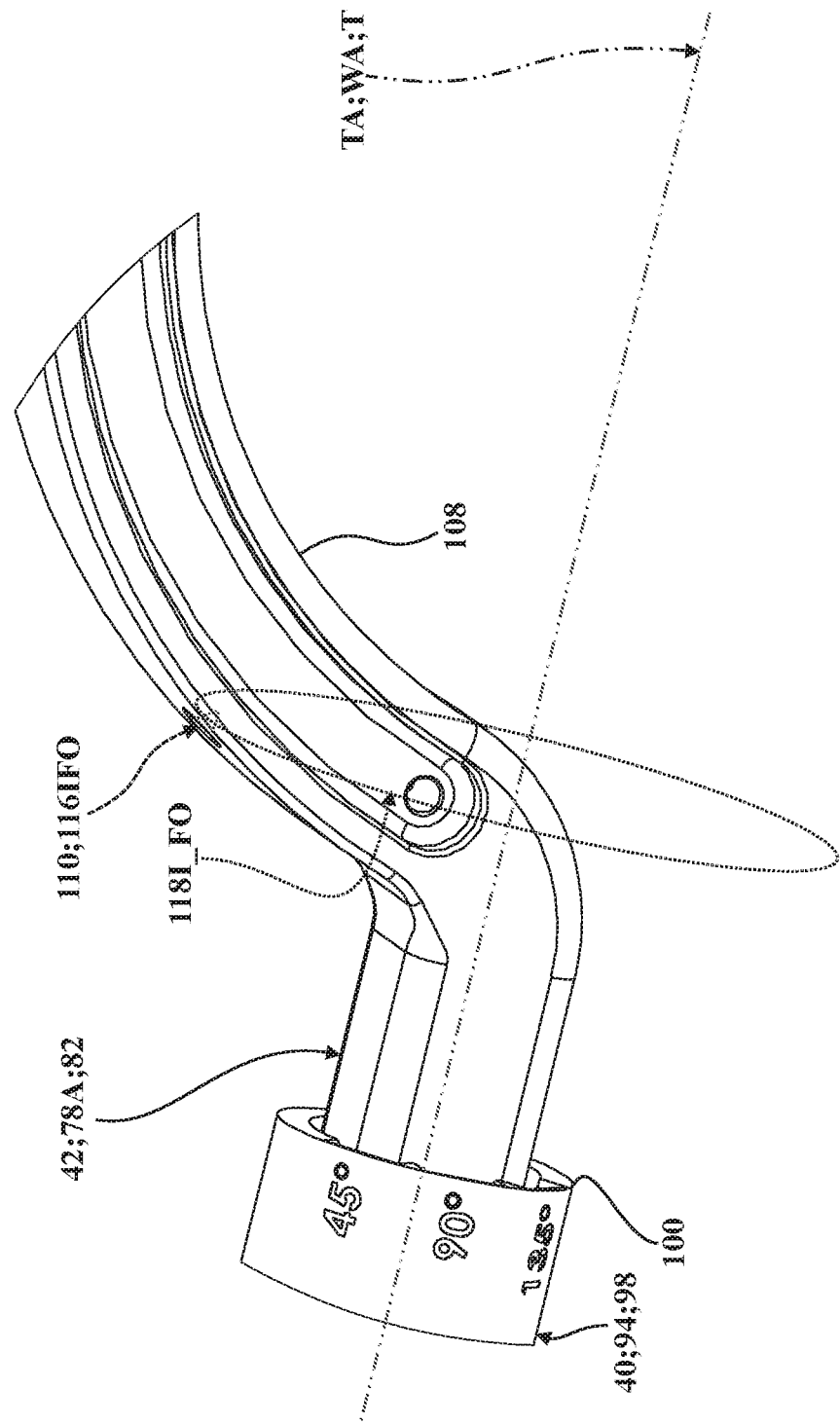

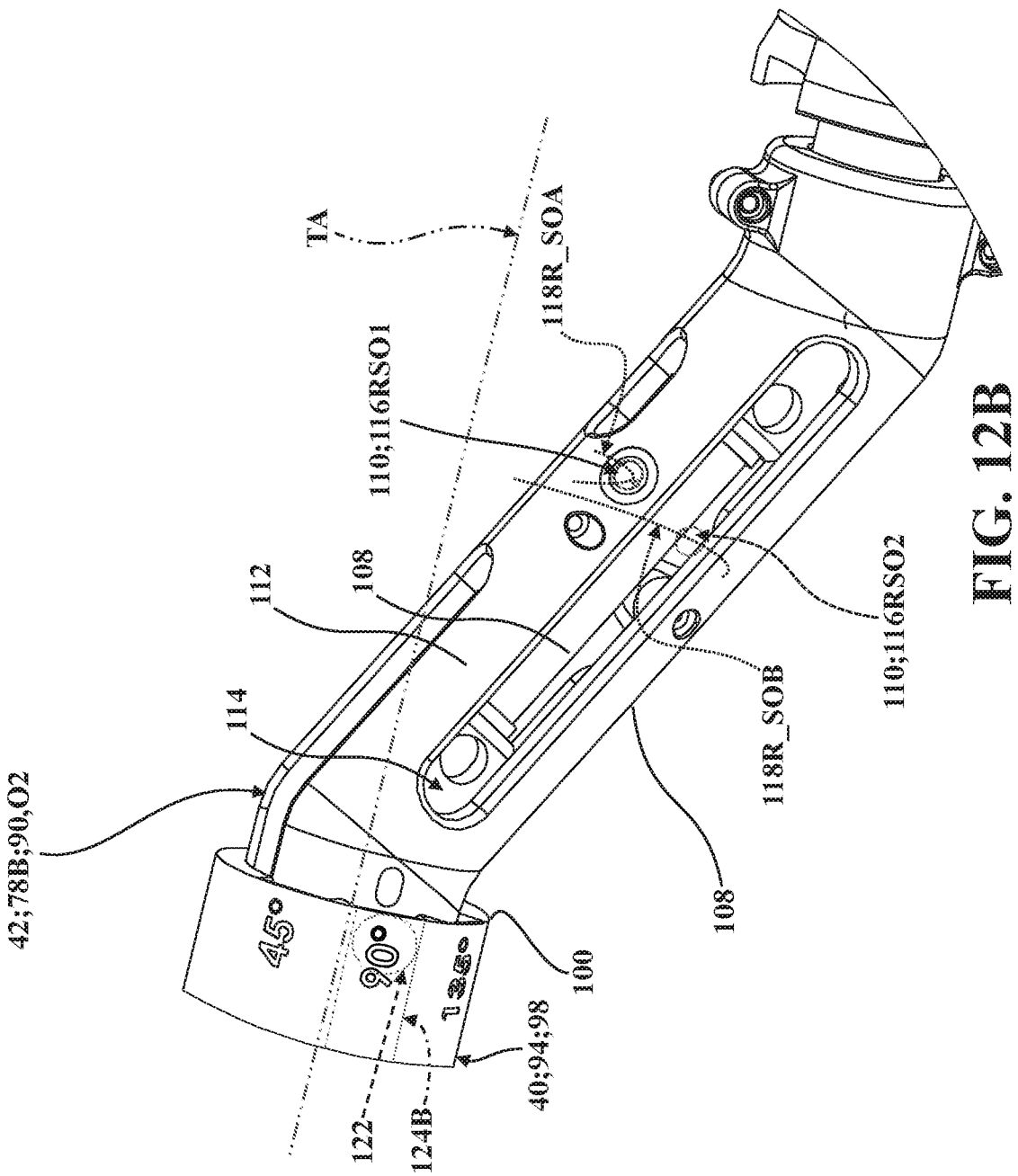

SURGICAL SYSTEMS AND METHODS FOR IDENTIFYING TOOLS GUIDED BY SURGICAL ROBOTS

CROSS-REFERENCE TO RELATED APPLICATION

The subject patent application claims priority to and all the benefits of U.S. Provisional Patent Application No. 62/631,995 filed on Feb. 19, 2018, the disclosure of which is hereby incorporated by reference in its entirety.

BACKGROUND

Surgical robots are frequently used to assist medical professionals in carrying out various conventional surgical procedures. To this end, a surgeon may use a surgical robot to guide, position, move, actuate, or otherwise manipulate various tools, components, prostheses, and the like during surgery.

It will be appreciated that surgical robots can be used to assist surgeons in performing a number of different types of surgical procedures. By way of illustrative example, surgical robots are commonly used in procedures involving the correction, resection, or replacement of degenerated joints to help improve patient mobility and reduce pain. For example, in hip replacement procedures, the surgeon replaces portions of the patient's hip joint with artificial prosthetic components. To this end, in total hip arthroplasty, the surgeon typically removes portions of the patient's femur to accommodate a prosthetic femoral component comprising a head, and resurfaces the acetabulum of the pelvis with a reamer to facilitate installing a prosthetic cup shaped to receive the head of the prosthetic femoral component.

Depending on the specific procedure being performed, the surgeon may attach different types of tools to the surgical robot to help facilitate approaching the surgical site, removing portions of joints and/or bone, installing prosthetic components, and the like. For example, an end effector which supports a reamer tool may be used to resurface the acetabulum of the pelvis, and an end effector which supports an impactor tool may be used to facilitate installing the prosthetic cup into the reamed acetabulum of the pelvis. Here, the surgical robot helps keep the reamer tool and the impactor tool aligned relative to the surgical site along a trajectory, and the surgeon closely monitors the trajectory and depth of reaming and impacting to ensure proper installation and alignment of the cup into the reamed acetabulum.

Depending on the configuration of the prosthetic components, the impaction tools, and the surgical robot, ensuring that the cup is implanted properly can be complicated by a lack of visibility and limited access to the surgical site. Moreover, maintaining a set trajectory can be difficult with certain approaches and surgical techniques. In order to accommodate different approaches and techniques, toolsets are provided to afford the surgeon with options for a particular type of tool. By way of example, a reamer toolset may comprise different sizes, shapes, and/or styles of reamer tools for the surgeon to select from for a particular surgical procedure, and an impactor toolset may comprise different sizes, shapes, and/or styles of impactor tools for the surgeon to select from for a particular surgical procedure.

Because different tools of a given toolset have respectively different configurations, the surgeon generally needs to input the selected tool's identity into one or more controllers in communication with the surgical robot so that the surgical robot can properly maintain the position, orientation, and/or trajectory of the tool with respect to the surgical site. Here, it will be appreciated that the process of properly inputting the identity of the selected tool into the controller takes time and may be susceptible to human error, such as where a toolset comprises a large number of visually-similar tools.

Accordingly, there remains a need in the art for addressing one or more of these deficiencies.

SUMMARY

The present disclosure provides a surgical system for assisting a user in performing a surgical procedure at a surgical site. The surgical system comprises a tool having a checkpoint feature, a pointer having a distal tip, and a localizer to determine a position of the pointer within a field of view. A memory is provided comprising identification data associated with a plurality of tools. The controller is configured to prompt the user to position the distal tip of the pointer at the checkpoint feature of the tool. The controller is also configured to receive position data from the localizer associated with the pointer within the field of view, and to compare position data associated with the pointer against the identification data of the memory to determine an identity of the tool. The controller is also configured to present the user with the identity of the tool.

The present disclosure also provides a toolset for driving a workpiece at a surgical site along a trajectory maintained by a surgical robot having a reference point. The toolset comprises a mount adapted to attach to the surgical robot, and a guide coupled to the mount and comprising a receiver. The toolset also comprises first and second tools. The first tool has a first working end to support the workpiece, a first coupling to engage the receiver of the guide, and a first tool body extending between the first working end and the first coupling with a first checkpoint feature arranged at a first predetermined location defined with respect to the reference point when the first coupling is engaged with the receiver and the mount is attached to the surgical robot. The second tool has a second working end to support the workpiece, a second coupling to engage the receiver of the guide, and a second tool body extending between the second working end and the second coupling with a second checkpoint feature arranged at a second predetermined location, different from the first predetermined location, defined with respect to the reference point when the second coupling is engaged with the receiver and the mount is attached to the surgical robot.

The present disclosure also provides a method of assisting a user in performing a surgical procedure with a surgical system comprising a surgical robot, a localizer, and a monitor. The method comprises: attaching a tool having a checkpoint feature to the surgical robot, and sending a first interface image to the monitor prompting the user to position a distal tip of the pointer at the checkpoint feature of the tool. The method also comprises tracking the pointer with the localizer to determine position data associated with the pointer, identifying the tool by comparing the position data from the localizer with stored identification data, and sending a second interface image to the monitor presenting the user with the identity of the tool.

Other features and advantages of the present disclosure will be readily appreciated, as the same becomes better understood, after reading the subsequent description taken in conjunction with the accompanying drawings.

BRIEF DESCRIPTION OF THE DRAWINGS

FIG. 3C is an exemplary third interface image to be displayed on the monitor of FIGS. 1-2, shown presenting an identity of the reamer tool alongside identities associated with other reamer tools of one toolset.

FIG. 6B is a partial, enlarged perspective view taken about indicia 6B in FIG. 6A, showing a checkpoint feature realized as a divot (partially shown in phantom) arranged about a circular checkpoint space.

FIG. 12B is a partial, enlarged perspective view taken about indicia 12B in FIG. 12A, showing the checkpoint features realized as divots (one divot shown in phantom) arranged along respective radial arc checkpoint spaces.

DETAILED DESCRIPTION

Figure 1:
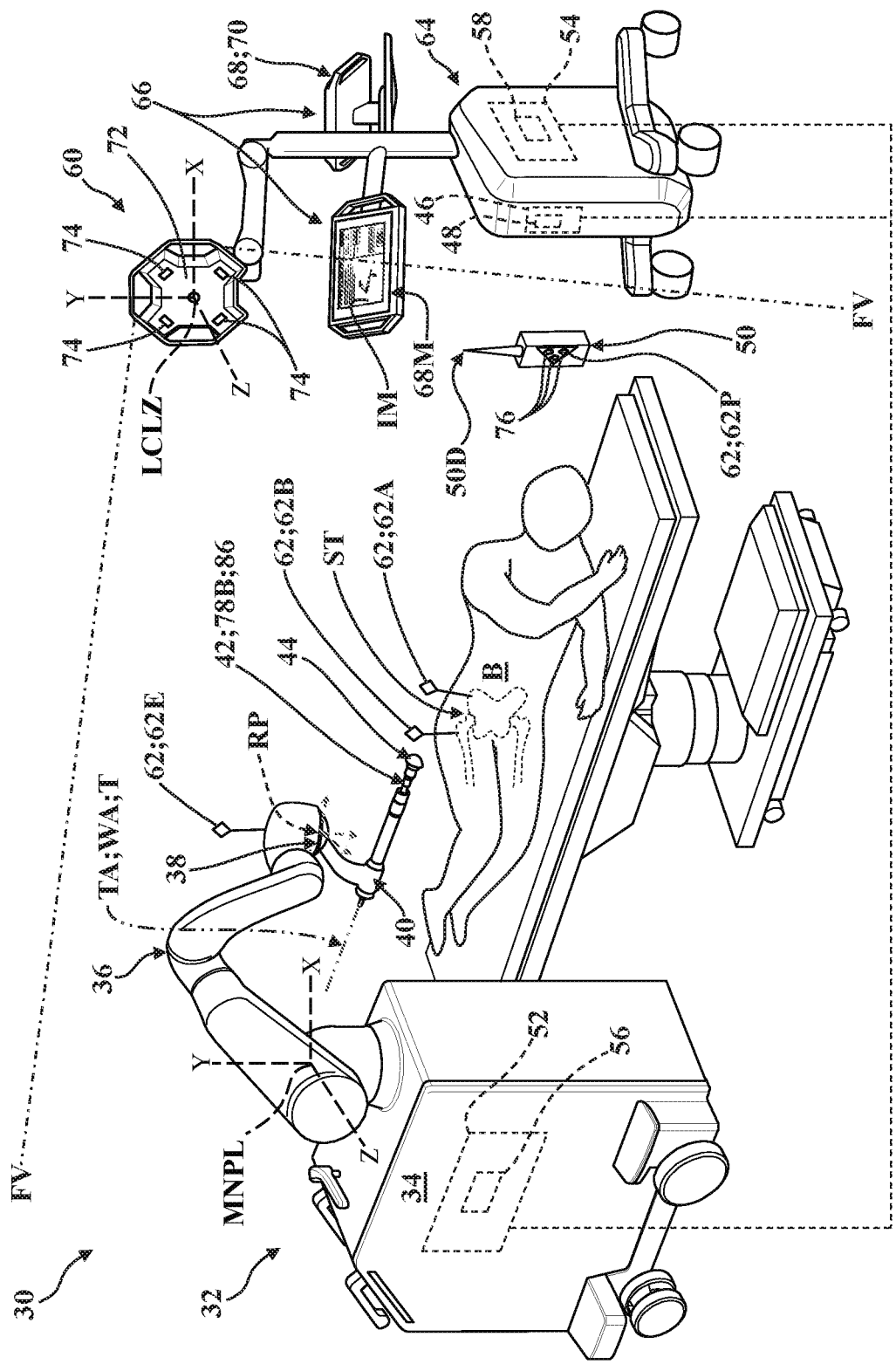
FIG. 1 is a perspective view of a surgical system comprising a surgical robot with a robotic arm supporting an end effector to which a tool is supported along a trajectory adjacent to a surgical site on a patient's body, and shown with a pointer, a localizer, and a monitor adjacent to the surgical robot.

Referring now to the drawings, wherein like numerals indicate like or corresponding parts throughout the several views, a surgical system 30 comprising a surgical robot 32 is shown in FIG. 1. The surgical robot 32 has a base 34, a robotic arm 36, and a coupler 38. As is described in greater detail below, the robotic arm 36 is supported by the base 34 and is configured to move, drive, maintain, or otherwise control the position and/or orientation of the coupler 38 relative to the base 34 during use. The coupler 38 is adapted to releasably secure an end effector 40 which, in turn, supports a tool, generally indicated at 42. The tool 42 is configured to support, position, or otherwise facilitate driving a workpiece, depicted generically at 44 in FIG. 1, at a surgical site ST on a patient's body B along a trajectory T maintained by the surgical robot 32. Thus, the surgical robot 32 moves the workpiece 44, the tool 42, and the end effector 40 via the robotic arm 36 to, among other things, assist medical professionals in carrying out various types of surgical procedures with precise control over movement and positioning of the end effector 40, the tool 42, and the workpiece 44. One exemplary arrangement of the robotic arm 36 is described in U.S. Pat. No. 9,119,655, entitled, "Surgical Robotic arm Capable of Controlling a Surgical Instrument in Multiple Modes," the disclosure of which is hereby incorporated by reference in its entirety. Another exemplary arrangement of the robotic arm 36 is described in U.S. Pat. No. 8,010,180, entitled, "Haptic Guidance System and Method," the disclosure of which is hereby incorporated by reference in its entirety. It will be appreciated that the robotic arm 36 and other portions of the surgical robot 32 may be arranged in alternative configurations.

While the workpiece 44 is depicted generically in FIG. 1, it will be appreciated that the tool 42 and/or the workpiece 44 could be of a number of different styles, types, and/or configurations, depending on the specific surgical procedure being performed. By way of non-limiting example, surgical procedures such as total hip arthroplasty routinely involve the use of multiple tools 42 to facilitate approaching the surgical site ST, preparing the surgical site ST, and/or installing implants (e.g., prosthetic components), and the like at the surgical site ST. In this illustrative example, one tool 42 could be a reamer used to facilitate preparing the acetabulum by driving a workpiece 44 realized as a reamer head (not shown in detail), and another tool 42 could be an impactor used to facilitate implanting a workpiece 44 realized as a prosthesis (not shown). The Applicant has described these types of reaming, preparing, and impaction processes in greater detail in U.S. Pat. Nos. 8,979,859 and 8,753,346, the disclosures of which are hereby incorporated by reference in their entirety. While the present disclosure describes various orthopedic procedures involving hip joints, it will be appreciated that the subject matter described herein may be applicable to other joints in the patient's body B, such as, for example, shoulders, elbows, wrists, spines, knees, ankles, and the like.

The surgical system 30 is able to monitor, track, and/or determine changes in the relative position and/or orientation of one or more parts of the surgical robot 32, the robotic arm 36, the end effector 40, the tool 42, and/or the workpiece 44, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the patient's anatomy), data from previous surgical procedures and/or previously-performed surgical techniques (e.g., data recorded while reaming the acetabulum that are subsequently used to facilitate impacting the prosthesis), and the like.

Figure 2:
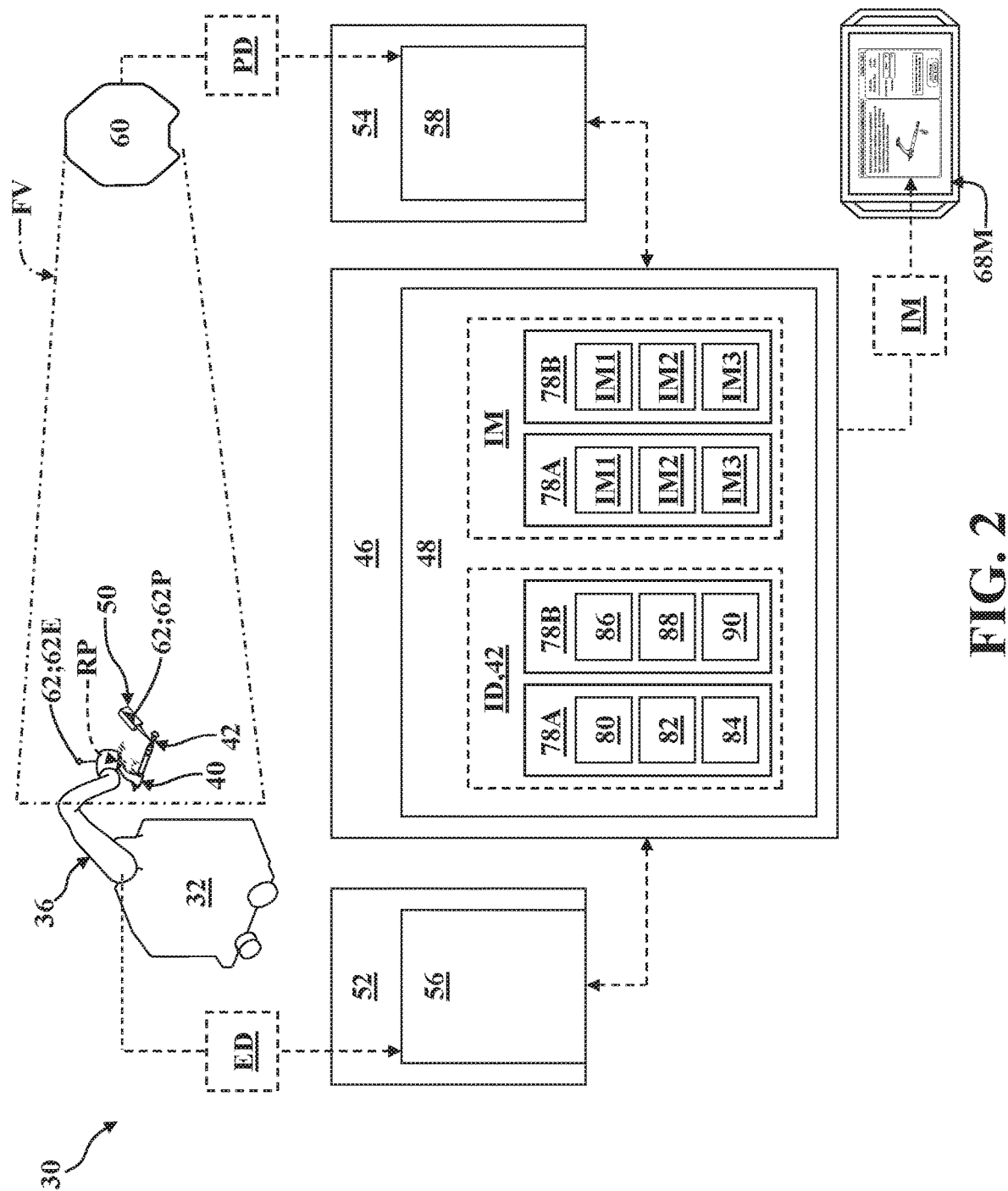
FIG. 2 is a schematic diagram of the surgical system shown having a controller in communication with the surgical robot, the localizer, and the monitor of FIG. 1.
Figure 3A:
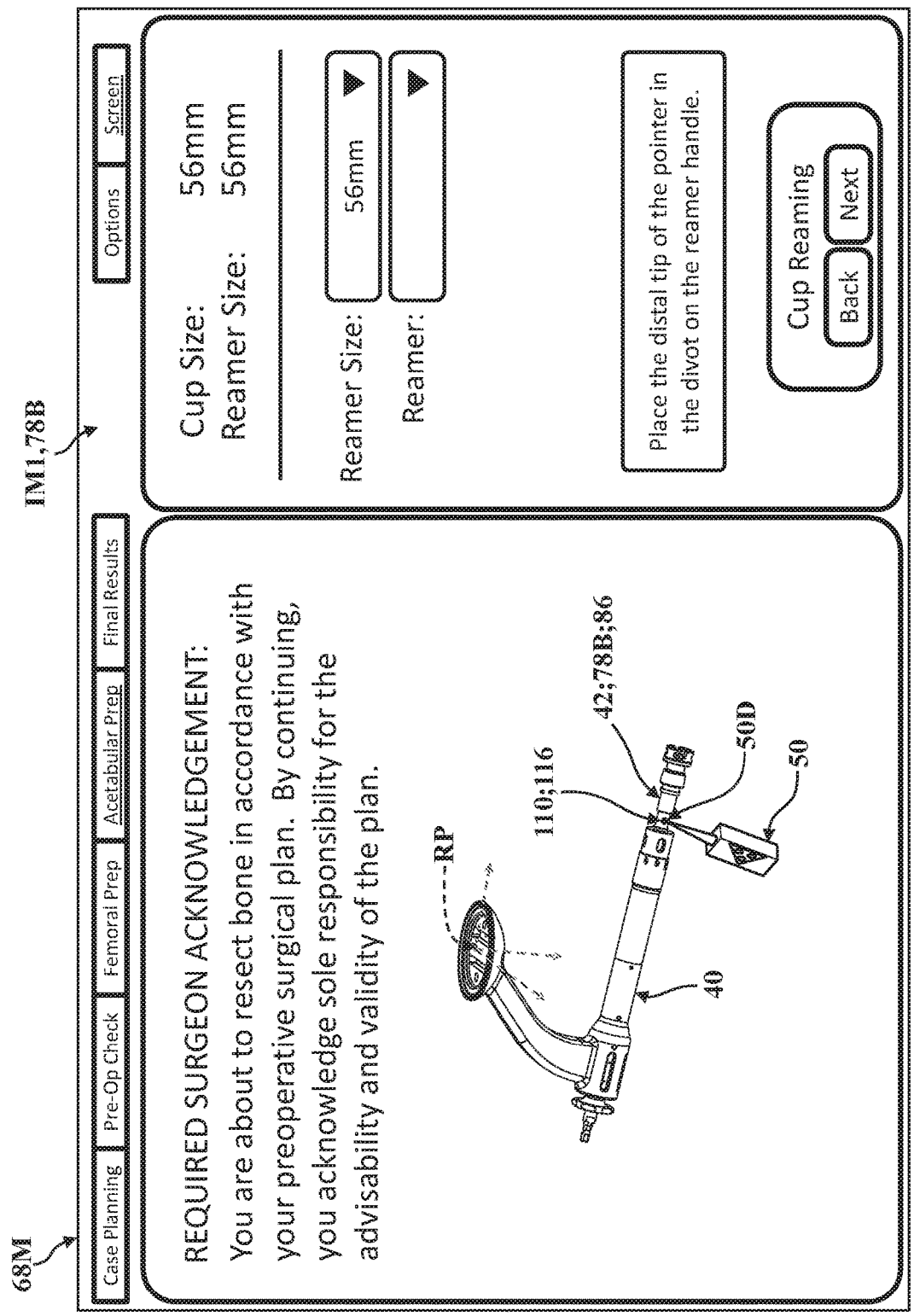
FIG. 3A is an exemplary first interface image to be displayed on the monitor of FIGS. 1-2, shown prompting a surgeon to place a distal top of the pointer of FIG. 1 in a divot formed in an end effector tool realized as a reamer.
Figure 3B:
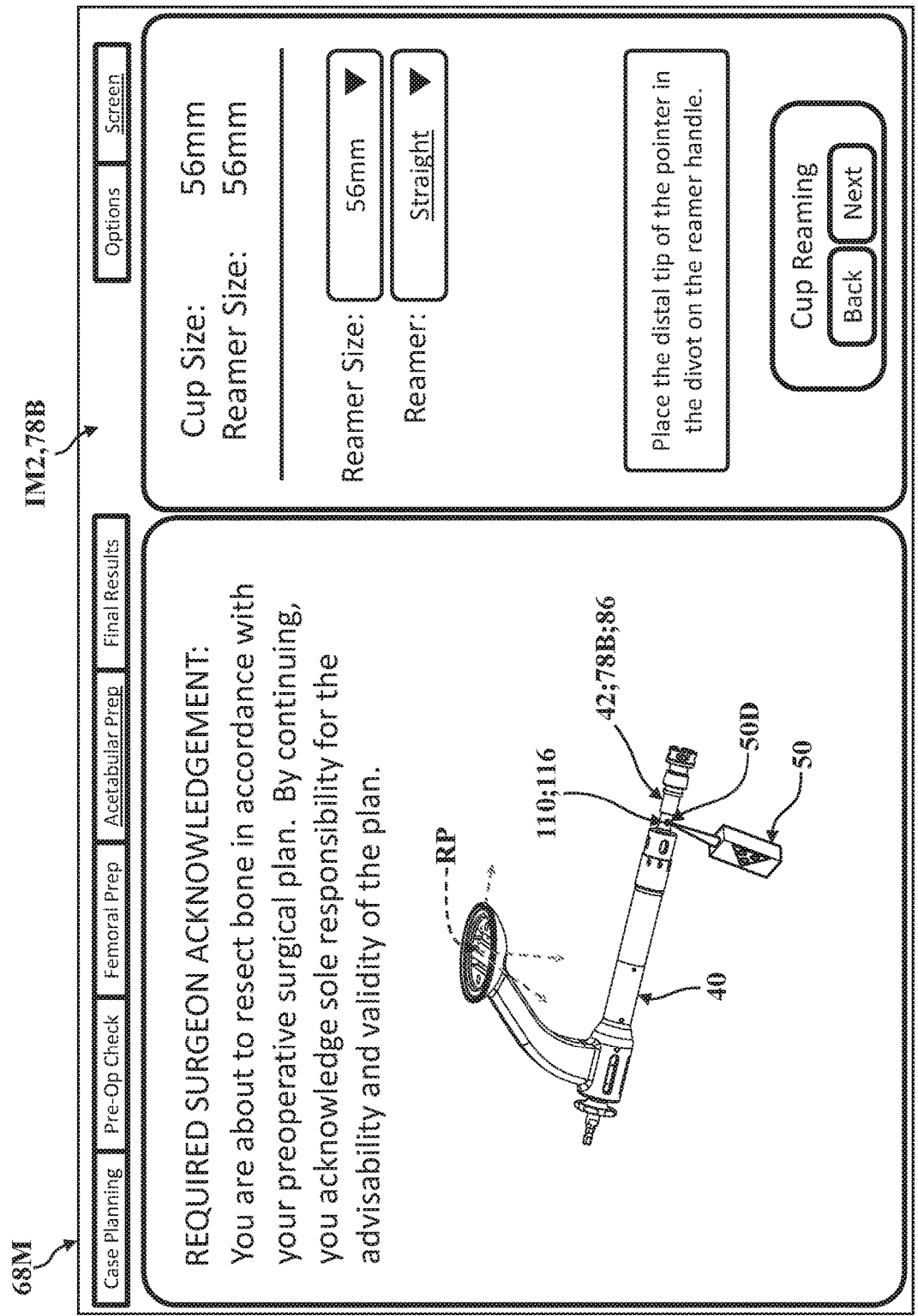
FIG. 3B is an exemplary second interface image to be displayed on the monitor of FIGS. 1-2, shown presenting an identity of the reamer tool.
Figure 4A:
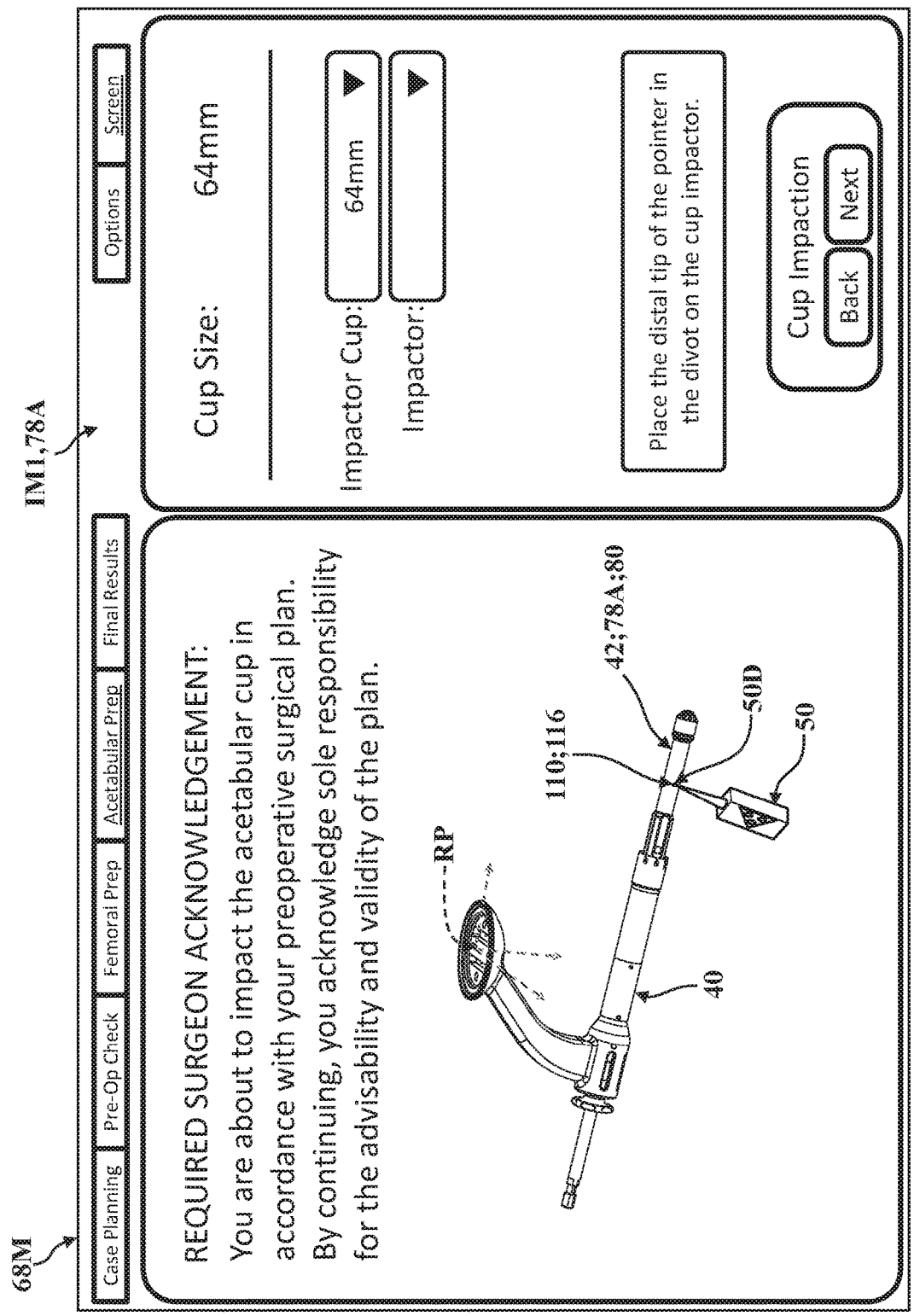
FIG. 4A is another exemplary first interface image to be displayed on the monitor of FIGS. 1-2, shown prompting a surgeon to place a distal top of the pointer of FIG. 1 in a divot formed in an end effector tool realized as an impactor.
Figure 4B:
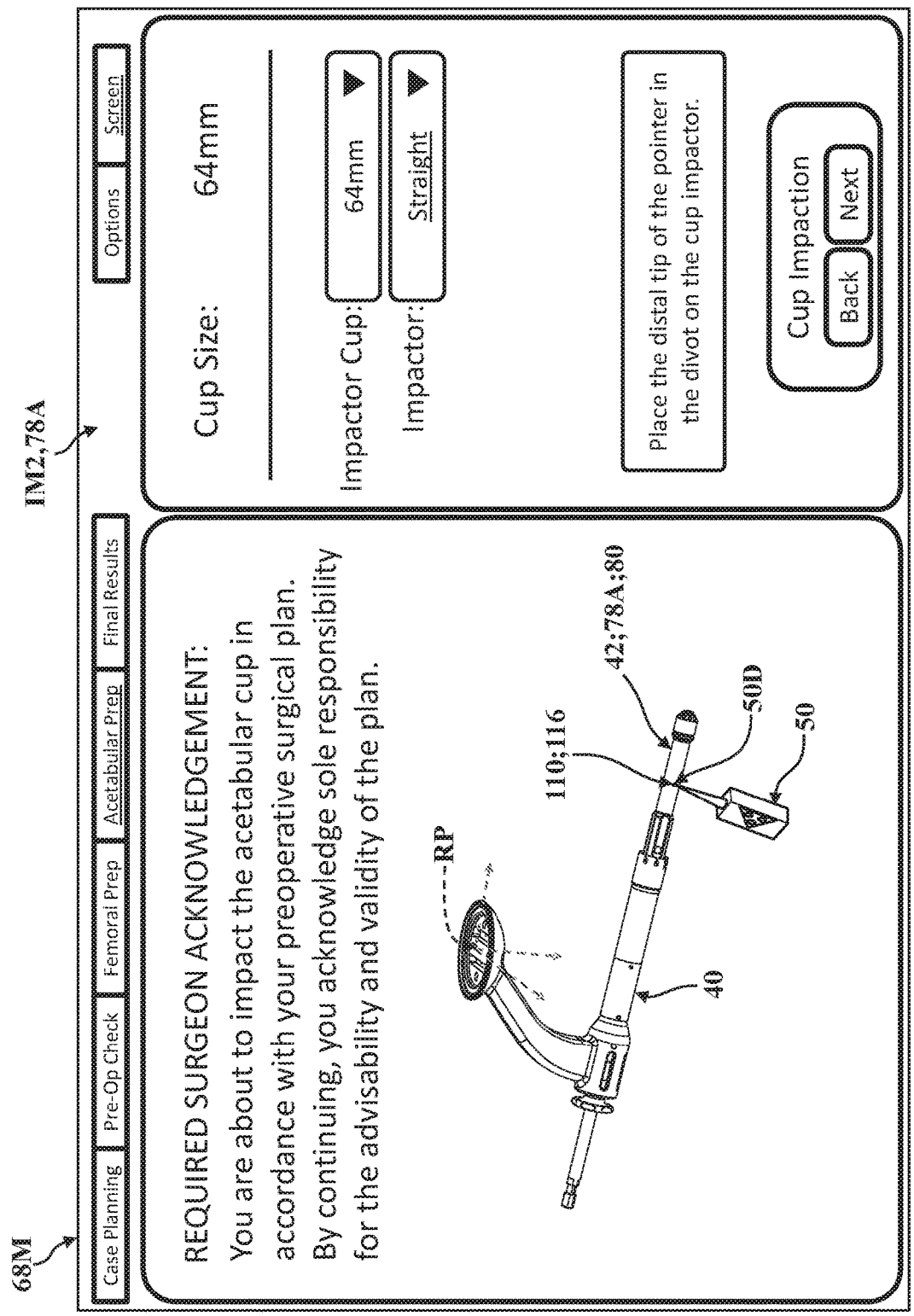
FIG. 4B is another exemplary second interface image to be displayed on the monitor of FIGS. 1-2, shown presenting an identity of the impactor tool.
Figure 4C:
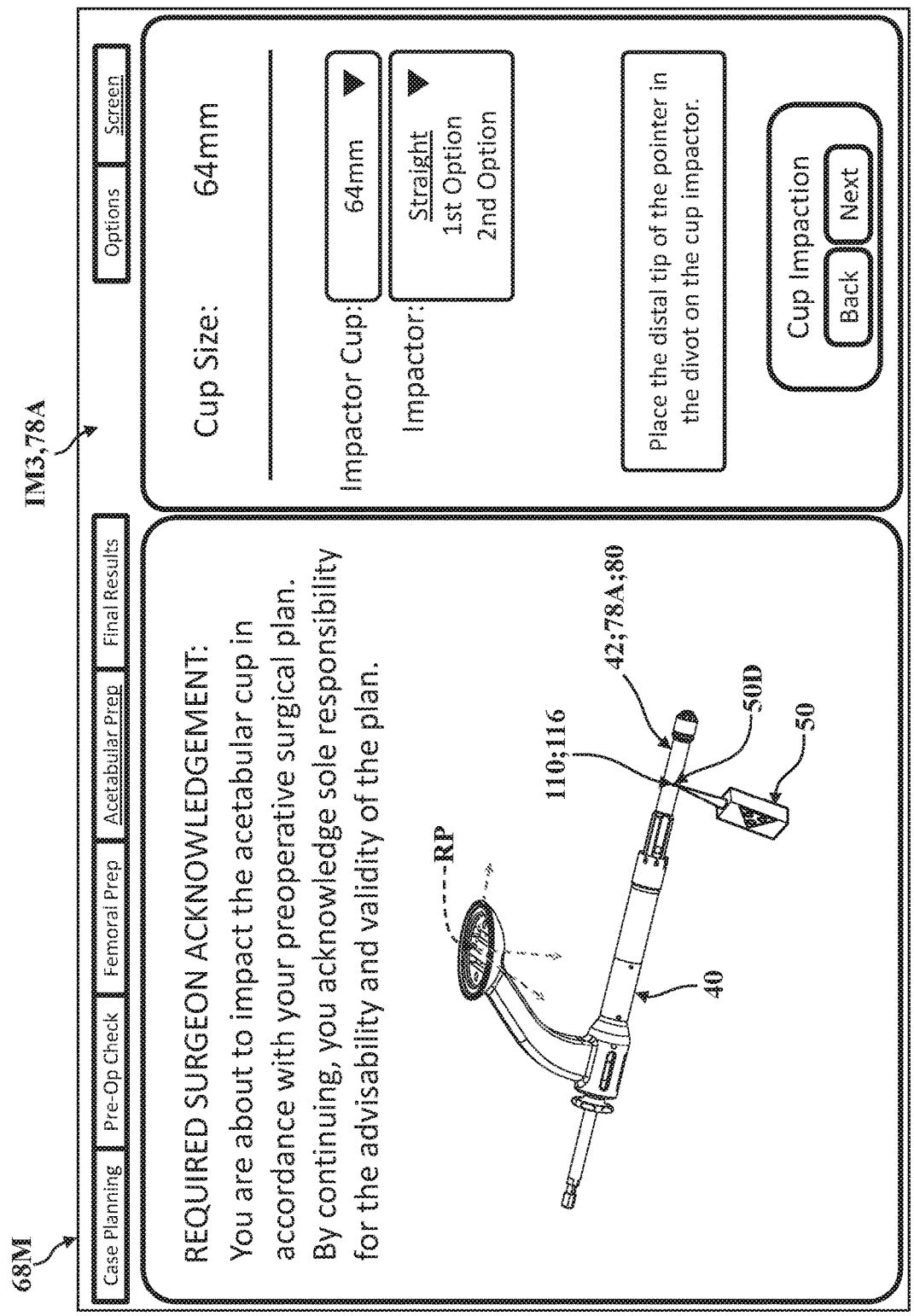
FIG. 4C is another exemplary third interface image to be displayed on the monitor of FIGS. 1-2, shown presenting an identity of the impactor tool alongside identities associated with other impactor tools of another toolset.

To these ends, and as is depicted schematically in FIGS. 1-2, the surgical system 30 generally comprises a controller 46, a memory 48 comprising identification data ID and interface images IM, a pointer 50 having a distal tip 50D, a robotic control system 52, and a navigation system 54 which cooperate to allow the surgical robot 32 maintain alignment of the tool 42 along the trajectory T. Each of these components will be described in greater detail below.

With continued reference to FIGS. 1-2, the controller 46 is disposed in communication with the robotic control system 52 and the navigation system 54, such as via wired or wireless electronic communication. In the illustrated embodiment depicted in FIG. 1, the controller 46 either communicates with or is realized by a robot controller 56 and/or a navigation controller 58, as described in greater detail below. The robot controller 56 forms part of the robotic control system 52, and the navigation controller 58 forms part of the navigation system 54. The controller 46, the robot controller 56, and/or the navigation controller 58 may be realized as computers, processors, control units, and the like, and may be discrete components, may be integrated, and/or may otherwise share hardware, software, inputs, outputs, and the like.

The surgical system 30 employs the robotic control system 52 to, among other things, articulate the robotic arm 36, maintain the trajectory T, and the like. Here, the robot controller 56 of the robotic control system 52 is configured to articulate the robotic arm 36 by driving various actuators, motors, and the like disposed at joints of the robotic arm 36 (not shown). The robot controller 56 also gathers data from various sensors such as encoders located along the robotic arm 36 (not shown). Because the specific geometry of each of the components of the surgical robot, end effector 40, and tools 42 are known, these sensor data can be used by the robot controller 56 to reliably adjust the position and/or orientation of the end effector 40 and the tool 42 within a manipulator coordinate system MNPL (see FIG. 1). The manipulator coordinate system MNPL has an origin, and the origin is located relative to the robotic arm 36. One example of this type of manipulator coordinate system MNPL is described in U.S. Pat. No. 9,119,655, entitled, "Surgical Robotic Arm Capable of Controlling a Surgical Instrument in Multiple Modes," previously referenced.

The surgical system 30 employs the navigation system 54 to, among other things, track movement of various objects such as the end effector 40, the pointer 50, and parts of the patient's body B (e.g. bones or other anatomy at the surgical site ST). To this end, the navigation system 54 employs a localizer 60 configured to sense the position and/or orientation of trackers 62 fixed to objects within a localizer coordinate system LCLZ. The navigation controller 58 is disposed in communication with the localizer 60 and gathers position and/or orientation data for each tracker 62 sensed within a field of view FV of the localizer 60 in the localizer coordinate system LCLZ. Thus, as is described in greater detail below, the localizer 60 is configured to determine a position of the tool 42 within the field of view FV.

It will be appreciated that the localizer 60 can sense the position and/or orientation of multiple trackers 62 to track correspondingly multiple objects within the localizer coordinate system LCLZ. By way of example, and as is depicted in FIG. 1, trackers 62 may comprise a pointer tracker 62P coupled to the pointer 50, an end effector tracker 62E coupled to the end effector 40, a first patient tracker 62A, and/or a second patient tracker 62B, as well as additional patient trackers, trackers for additional medical and/or surgical tools, and the like. In FIG. 1, the end effector tracker 62E is firmly affixed to the end effector 40, the first patient tracker 62A is firmly affixed to one bone of the patient's body B at the surgical site ST (e.g., to the pelvis adjacent to the acetabulum), and the second patient tracker 62B is firmly affixed to a different bone (e.g., to the femur adjacent to the head). The end effector tracker 62E could be fixed to the end effector 40 in different ways, such as by integration into the end effector 40 during manufacture or by releasable attachment to the end effector 40. The patient trackers 62A, 62B are firmly affixed to different bones in the patient's body B, such as by threaded engagement, clamping, or by other techniques. It will be appreciated that various trackers 62 may be firmly affixed to different types of tracked objects (e.g., discrete bones, tools, pointers, and the like) in a number of different ways.

The position of the trackers 62 relative to the anatomy to which they are attached can be determined by known registration techniques, such as point-based registration in which the distal tip 50D of the pointer 50 is used to touch off on bony landmarks on bone or to touch off on several points across the bone for surface-based registration as the localizer 60 monitors the position and orientation of the pointer tracker 62P. Conventional registration techniques can then be employed to correlate the pose of the patient trackers 62A, 62B to the patient's anatomy (e.g., to each of the femur and acetabulum). Other types of registration are also possible, such as by using patient trackers 62A, 62B with mechanical clamps that attach to bone and have tactile sensors (not shown) to determine a shape of the bone to which the clamp is attached. The shape of the bone can then be matched to a 3D model of bone for registration. A known relationship between the tactile sensors and the three or more markers on the patient tracker 62A, 62B may be entered into or otherwise known by the navigation controller 58. Based on this known relationship, the positions of the markers relative to the patient's anatomy can be determined.

Position and/or orientation data may be gathered, determined, or otherwise handled by the navigation controller 58 using conventional registration/navigation techniques to determine coordinates of each tracker 62 within the localizer coordinate system LCLZ. These coordinates are communicated to the robotic control system 52 to facilitate articulation of the robotic arm 36 and/or to otherwise assist the surgeon in performing the surgical procedure, as described in greater detail below.

In the representative embodiment illustrated in FIG. 1, the robot controller 56 is operatively attached to the surgical robot 32, and the navigation controller 58, the localizer 60, the controller 46, and the memory 48 are supported on a mobile cart 64 which is movable relative to the base 34 of the surgical robot 32. The mobile cart 64 also supports a user interface, generally indicated at 66, to facilitate operation of the surgical system 30 by displaying information to, and/or by receiving information from, the surgeon or another user. The user interface 66 is disposed in communication with the controller 46, the memory 48, the navigation system 54, and/or the robotic control system 52, and may comprise one or more output devices 68 (e.g., monitors, indicators, display screens, and the like) to present information to the surgeon (e.g., images, video, data, a graphics, navigable menus, and the like), and one or more input devices 70 (e.g., buttons, touch screens, keyboards, mice, gesture or voice-based input devices, and the like). In the illustrated embodiment, the user interface 66 comprises an output device 68 realized as a monitor 68M to display interface images IM, as described in greater detail below. One type of mobile cart 64 and user interface 66 is described in U.S. Pat. No. 7,725,162, entitled "Surgery System," the disclosure of which is hereby incorporated by reference in its entirety.

Because the mobile cart 64 and the base 34 of the surgical robot 32 can be positioned relative to each other and also relative to the patient's body B, the surgical system 30 transforms the coordinates of each tracker 62 within the field of view FV from the localizer coordinate system LCLZ into the manipulator coordinate system MNPL, or vice versa, so that articulation of the robotic arm 36 can be performed based at least partially on the relative positions and orientations of each tracker 62 within a single, common coordinate system (the manipulator coordinate system MNPL, the localizer coordinate system LCLZ, or another common coordinate system). It will be appreciated that coordinates within the localizer coordinate system LCLZ can be transformed into coordinates within the manipulator coordinate system MNPL, and vice versa, using a number of different conventional coordinate system transformation techniques.

In the illustrated embodiment, the localizer 60 is an optical localizer and includes a camera unit 72 with one or more optical position sensors 74. The navigation system 54 employs the optical position sensors 74 of the camera unit 72 to sense the position and/or orientation of the trackers 62 within the localizer coordinate system LCLZ. In the representative embodiment illustrated herein, the trackers 62 each employ markers 76 which can be sensed by the optical position sensors 74 of the camera unit 72. One example of a navigation system 54 of this type is described in U.S. Pat. No. 9,008,757, entitled, "Navigation System Including Optical and Non-Optical Sensors," the disclosure of which is hereby incorporated by reference in its entirety. In some embodiments, the markers 76 are active markers (e.g., light emitting diodes "LEDs") which emit light that is sensed by the optical position sensors 74. In other embodiments, the markers 76 may be passive markers (e.g., reflectors) which reflect light emitted from the camera unit 72 or another light source. It should be appreciated that other suitable tracking systems and methods not specifically described herein may be utilized (e.g., ultrasonic, electromagnetic, radio frequency, and the like).

In some embodiments, the surgical system 30 is capable of displaying a virtual representation of the relative positions and orientations of tracked objects to the surgeon or other users of the surgical system 30, such as with images and/or graphical representations of the anatomy of the patient's body B, the end effector 40, and/or the tool 42 presented on one or more output devices 68, such as the monitor 68M. The controller 46, the robot controller 56, and/or navigation controller 58 may also utilize the user interface 66 to display instructions or request information such that the surgeon or other users may interact with the robotic control system 52 to facilitate articulation of the robotic arm 36. By way of example, the controller 46 is configured to send different interface images IM stored in the memory 48 to the monitor 68M as described in greater detail below. Other configurations are contemplated.

It will be appreciated that the robotic control system 52 and the navigation system 54 can cooperate to facilitate control over the position and/or orientation of the end effector 40 and/or tool 42 in different ways. By way of example, in some embodiments, the robot controller 56 is configured to control the robotic arm 36 (e.g., by driving joint motors) to provide haptic feedback to the surgeon via the robotic arm 36. Here, haptic feedback helps constrain or inhibit the surgeon from manually moving the end effector 40 and/or tool 42 beyond predefined virtual boundaries associated with the surgical procedure (e.g., to maintain alignment of the tool 42 along the trajectory T). One type of haptic feedback system and associated haptic objects that define virtual boundaries are described, for example, in U.S. Pat. No. 8,010,180, "entitled, "Haptic Guidance System and Method," the disclosure of which is hereby incorporated by reference in its entirety. In one embodiment, the surgical system 30 is the RIO™ Robotic Arm Interactive Orthopedic System manufactured by MAKO Surgical Corp. of Fort Lauderdale, Fla., USA.

Referring now to FIGS. 1-14, as noted above, the surgical system 30 employs the end effector 40 to position the tool 42 at the surgical site ST along the trajectory T maintained by the surgical robot 32 to assist the surgeon in carrying out various types of surgical procedures with precise control over the relative position and orientation of the workpiece 44 attached to the tool 42 with respect to the patient's body B. Those having ordinary skill in the art will appreciate that different types of surgical procedures routinely involve the use of a number of different types of surgical devices, tools, and the like. Thus, for surgical procedures carried out in connection with surgical robots 32, different end effectors 40 and/or tools 42, of various types, sizes, and/or configurations, may be utilized during a single surgical procedure. Here, the surgical system 30 is configured so as to allow the surgeon to attach different types of end effectors 40 and/or tools 42 to the coupler 38 of the surgical robot 32, and also to allow the surgeon to select between variations of the same type of end effector 40 and/or tool 42. To this end, and in the representative embodiment illustrated herein, the surgical system 30 comprises first and second toolsets 78A, 78B, each of which includes first, second, and third tools 42 which, as described in greater detail below, are variations of the same general type of tool 42.

Figure 5A:
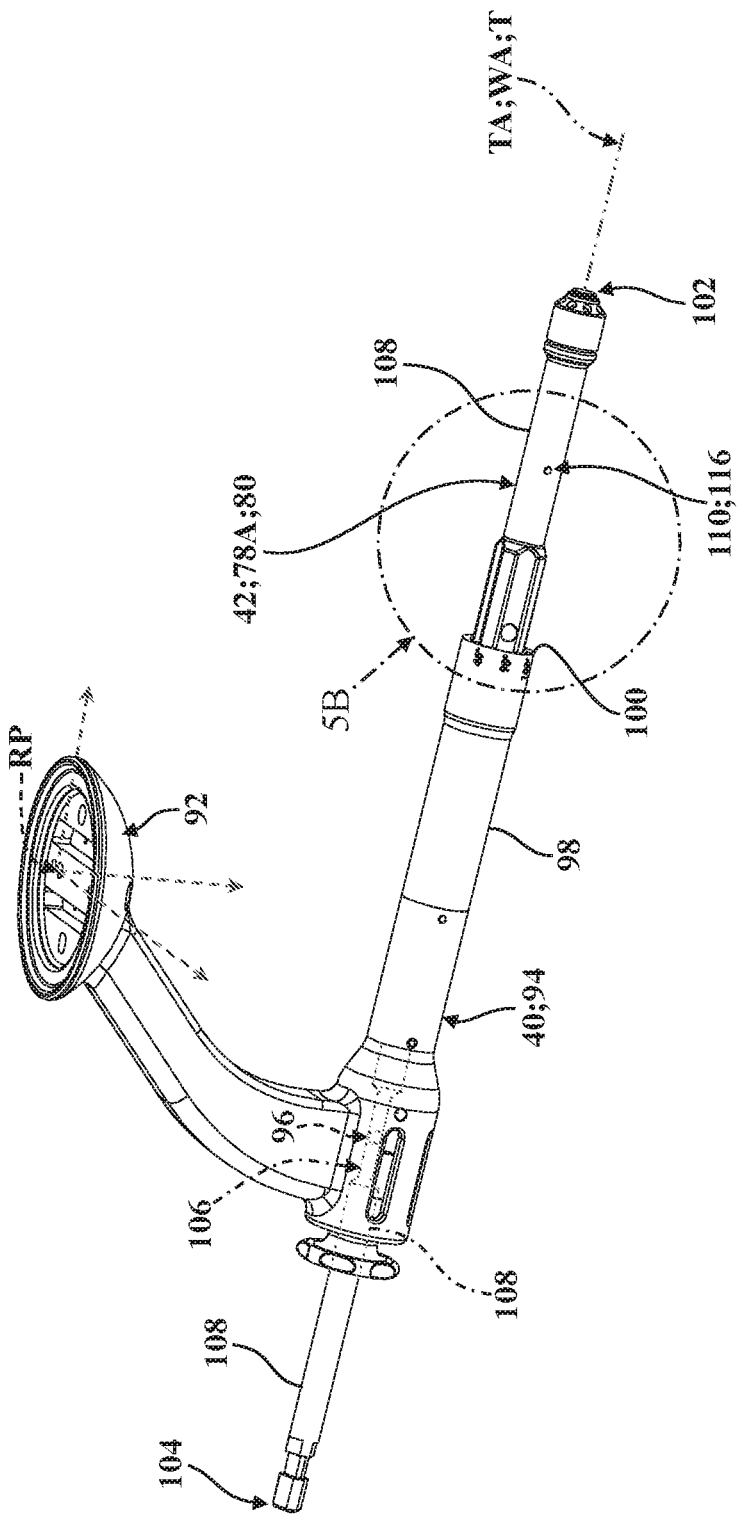
FIG. 5A is a perspective view of an end effector with a tool realized as a straight impactor for use with the surgical system of FIG. 1.
Figure 5B:
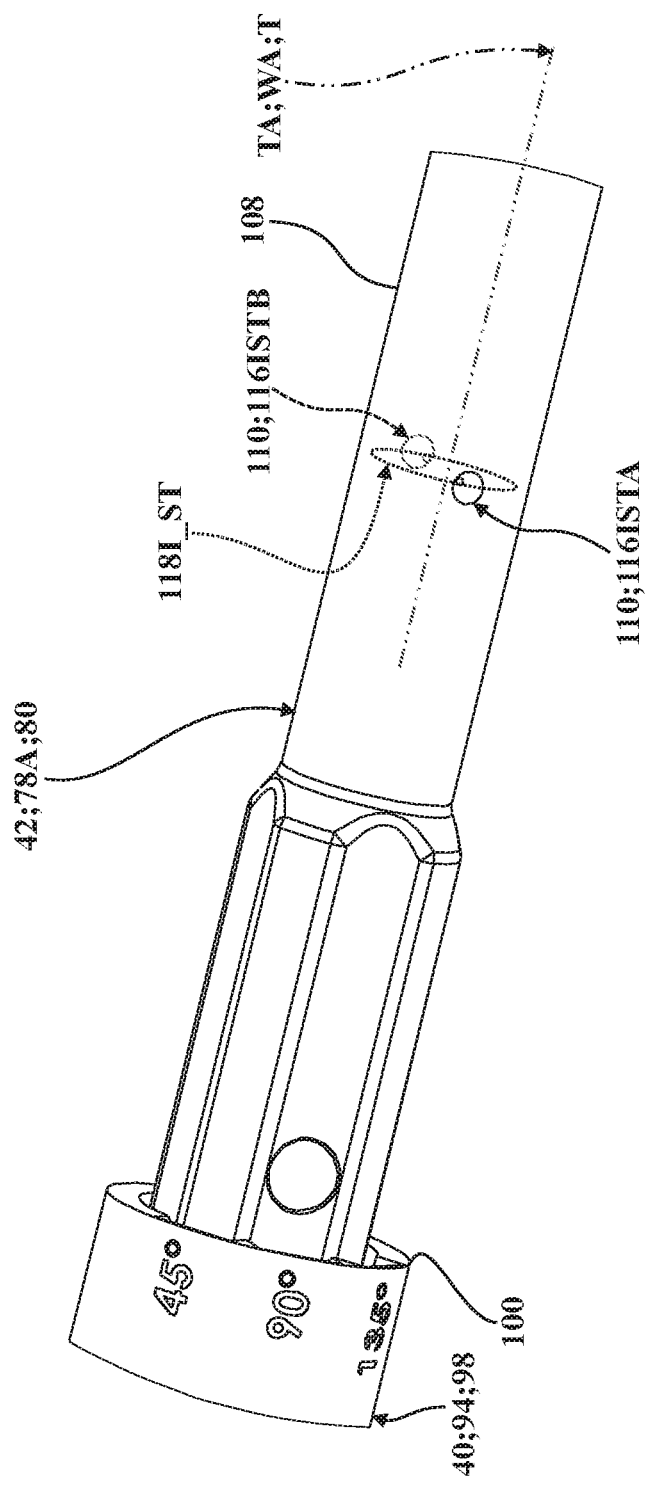
FIG. 5B is a partial, enlarged perspective view taken about indicia 5B in FIG. 5A, showing checkpoint features realized as divots (one divot shown in phantom) arranged about a circular checkpoint space.
Figure 6A:
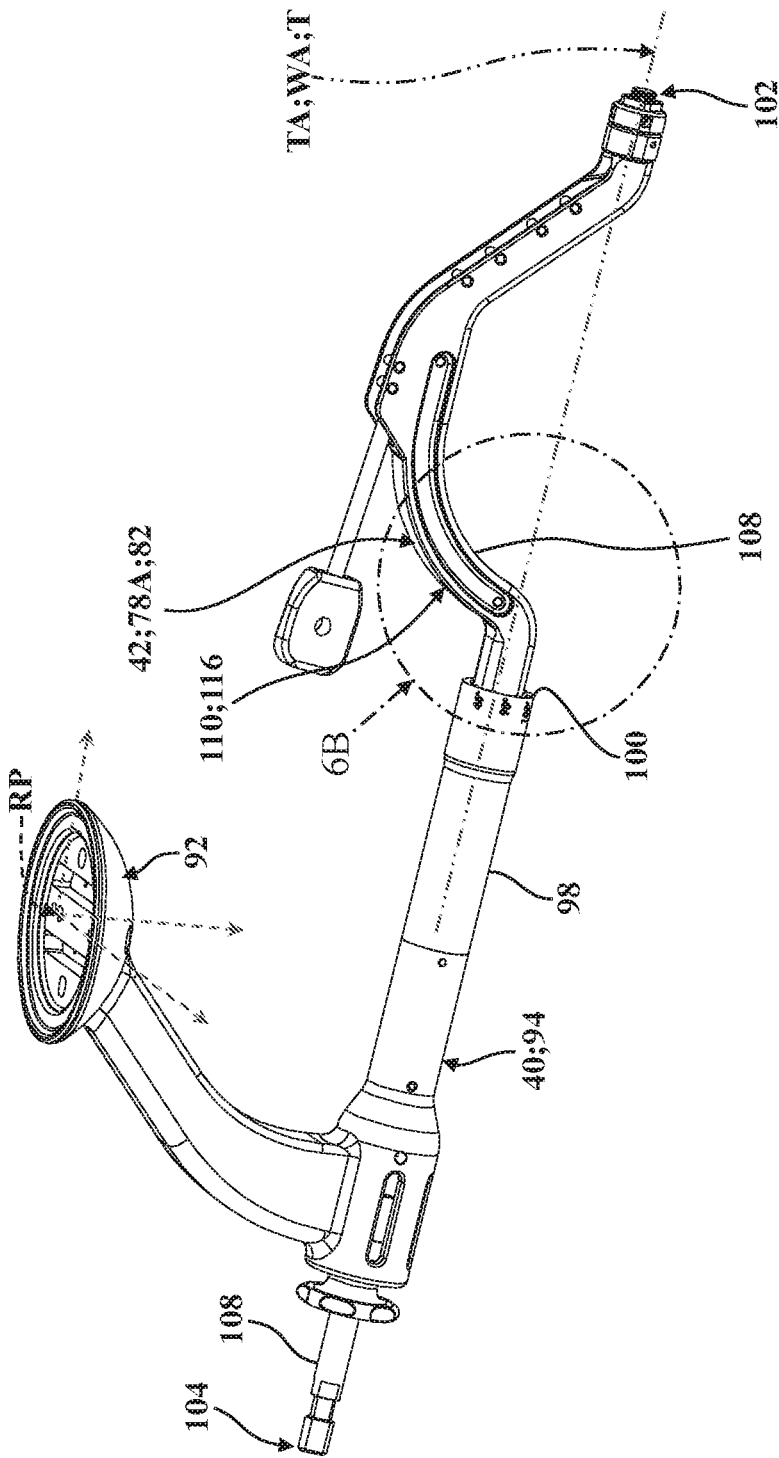
FIG. 6A is a perspective view of an end effector with a tool realized as a first-option impactor for use with the surgical system of FIG. 1.
Figure 7A:
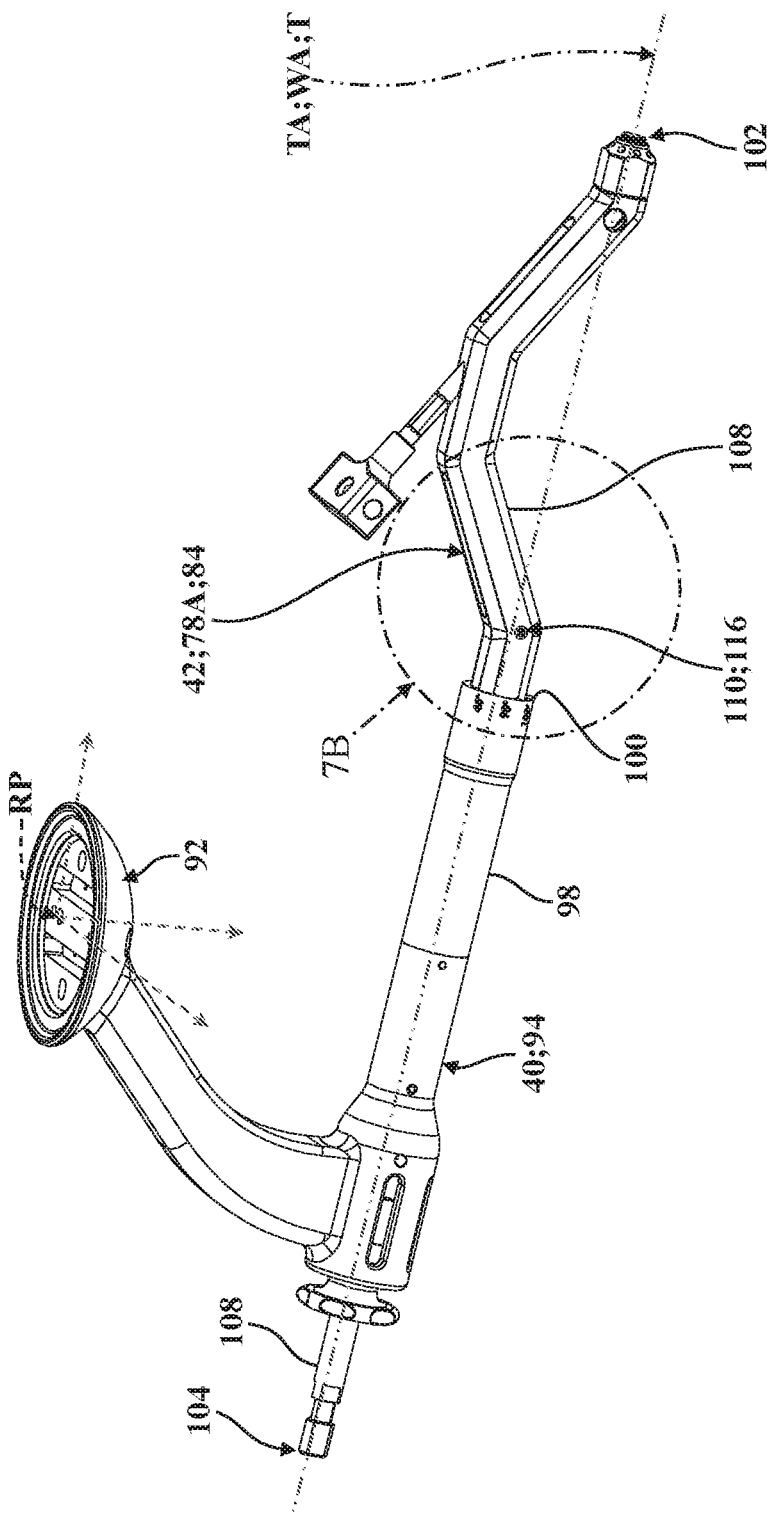
FIG. 7A is a perspective view of an end effector with a tool realized as a second-option impactor for use with the surgical system of FIG. 1.
Figure 7B:
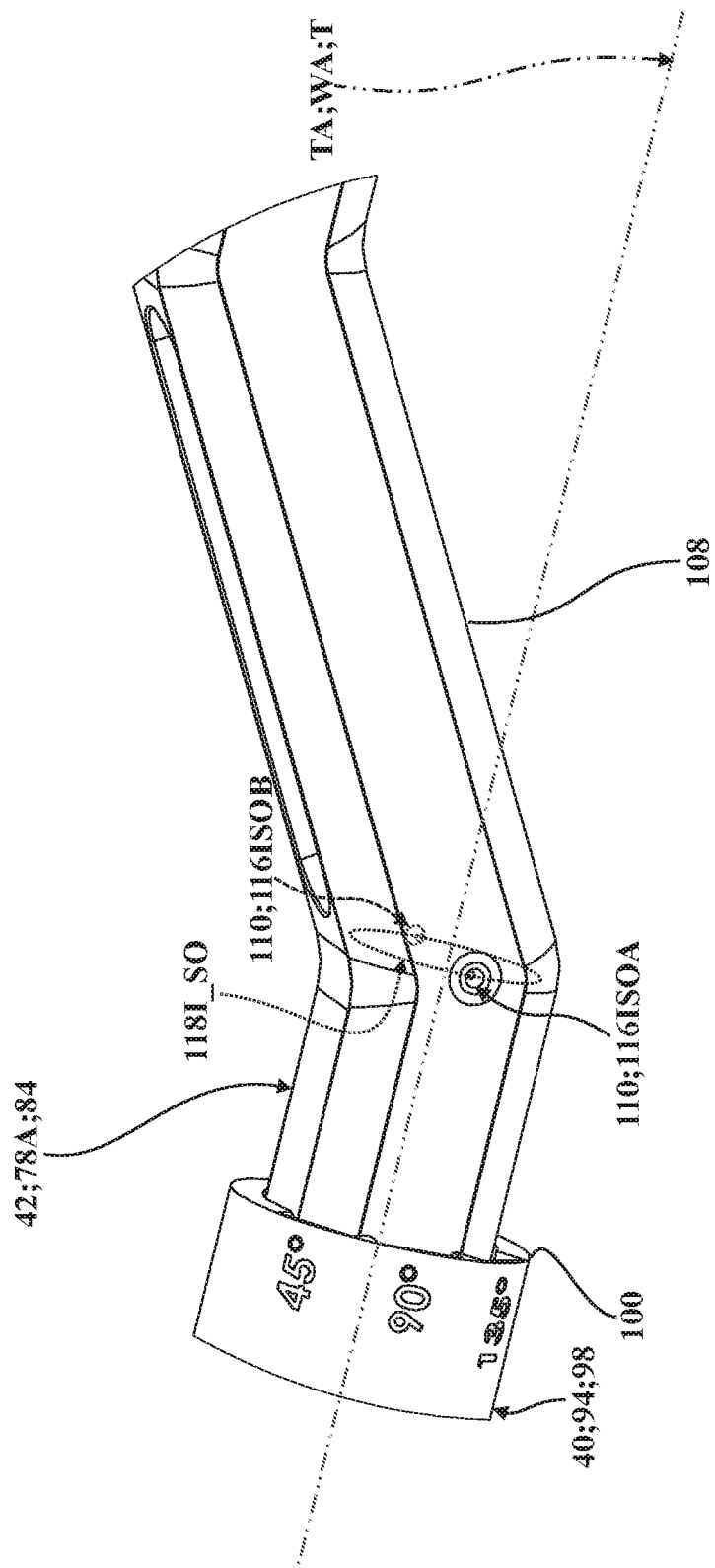
FIG. 7B is a partial, enlarged perspective view taken about indicia 7B in FIG. 7A, showing checkpoint features realized as divots (one divot shown in phantom) arranged about a circular checkpoint space.

FIGS. 5A-8 generally depict the first toolset 78A, which includes first, second, and third variations of tools 42 configured as impactors: a straight impactor 80 (see FIGS. 5A-5B), a first-option impactor 82 (see FIGS. 6A-6B), and a second-option impactor 84 (see FIGS. 7A-7B). Furthermore, FIGS. 9A-14 generally depict the second toolset 78B, which includes first, second, and third variations of tools 42 configured as reamers: a straight reamer 86 (see FIGS. 9A-9B), a first-option reamer 88 (see FIGS. 10A-10B), and a second-option reamer 90 (see FIGS. 11A-13B). It will be appreciated that the types of first and second toolsets 78A, 78B illustrated and described herein, as well as the variations 80, 82, 84; 86, 88, 90 of tools 42 in the toolsets 78A, 78B, are exemplary and non-limiting. Thus, while the present disclosure is directed toward an impactor toolset 78A and a reamer toolset 78B each having three variations 80, 82, 84; 86, 88, 90 of tools 42, other configurations are contemplated and the surgical system 30 could comprise any suitable number of toolsets each having any suitable number of variations of tools 42 configured for use in any type of surgical procedure where surgical robots 32 are employed.

Those having ordinary skill in the art will appreciate that the variations 80, 82, 84; 86, 88, 90 of tools 42 within the toolsets 78A, 78B affords the surgeon with flexibility in carrying out different types of surgical procedures in different ways. By way of non-limiting example, the surgeon may select a variation 80, 82, 84; 86, 88, 90 of one or more types of tools 42 to facilitate a particular approach, improve visibility of the surgical site ST, accommodate handling and/or orientation preferences, and the like. While this flexibility is advantageous, variations 80, 82, 84; 86, 88, 90 of tools 42 generally position workpieces 44 (e.g., a prosthetic cup for the impactors 80, 82, 84, and a reamer head for the reamers 86, 88, 90) in different ways with respect to the coupler 38 of the surgical robot 34. As is described in greater detail below, the controller 46 cooperates with the memory 48, the pointer 50, the localizer 60, and the monitor 68M to ensure that the surgical system 30 can distinguish between variations 80, 82, 84; 86, 88, 90 of tools 42 and thereby determine the position and orientation of the workpiece 44 based on the identity of the tool 42 being utilized.

Referring now to FIGS. 5A-14, the illustrated tools 42 are each configured for releasable attachment to a common end effector 40. Put differently, in one embodiment, the end effector 40 is configured to releasably secure the straight impactor 80 (see FIG. 5A), the first-option impactor 82 (see FIG. 6A), the second-option impactor 84 (see FIG. 7A), the straight reamer 86 (see FIG. 9A), the first-option reamer 88 (see FIG. 10A), and/or the second-option reamer 90 (see FIGS. 11A, 12A, and 13A). While this configuration advantageously allows the surgeon to quickly change between different tools 42 without detaching the end effector 40 from the coupler 38 of the surgical robot 32, it will be appreciated that each toolset 78A, 78B or even each individual tool 42 could be provided with its own end effector 40 in certain embodiments.

In order to facilitate releasable attachment of the tools 42 to the end effector 40, the end effector 40 generally comprises a mount 92, a guide 94, and a receiver 96. The mount 92 is adapted to releasably attach to the coupler 38 of the surgical robot 32 (see FIG. 1). The guide 94 is coupled to the mount 92 and comprises the receiver 96 which, in turn, is configured to releasably secure the tool 42 to the guide 94. Examples of this type of guide 94 and receiver 96 are described in U.S. Pat. No. 8,753,346, previously referenced.

The guide 94 has a generally cylindrical region 98 which defines a tool axis TA and extends to a distal guide end 100. The receiver 96 (depicted schematically as a sphere in FIGS. 5A and 9A) is configured to restrict movement of the tool 42 relative to the guide 94 in different ways depending on the type of tool 42. By way of illustrative example, the receiver 96 is generally configured to permit free rotation of the impactors 80, 82, 84 about the tool axis TA, and to permit limited translation along the tool axis TA (not shown in detail). By way of further illustrative example, the receiver 96 is generally configured to inhibit translation of the reamers 86, 88, 90 along the tool axis TA (see FIGS. 5A, 6A, and 7A), to permit free rotation of the straight reamer 86 and the first-option reamer 88 about the tool axis TA (see FIGS. 9A and 10A), and to permit selective positioning of the second-option reamer 90 about the tool axis TA between first, second, and third orientations O1, O2, O3 (see FIGS. 11A, 12A, and 13A) as described in greater detail below.

The tools 42 each generally comprise a respective working end 102, a proximal end 104, a coupling 106, a tool body 108, and a checkpoint feature 110. The working end 102 is configured to releasably secure and support the workpiece 44 (e.g., a prosthetic cup for the impactors 80, 82, 84, and a reamer head for the reamers 86, 88, 90). The coupling 106 of the tool 42 (depicted schematically as an elongated recess in FIG. 5A and as an indent in FIG. 9A) is formed in the tool body 110 and is configured to engage the receiver 96 of the guide 94 of the end effector 40 to restrict or inhibit axial translation of the tool 42, as noted above. The tool body 108 extends between the working end 102 and the proximal end 104, with the coupling 106 arranged adjacent to the proximal end 104. The checkpoint feature 110 is generally formed in the tool body 108, and is arranged relative to a common reference point RP at a predetermined location that is specific to each tool 42, as described in greater detail below.

Figure 10A:
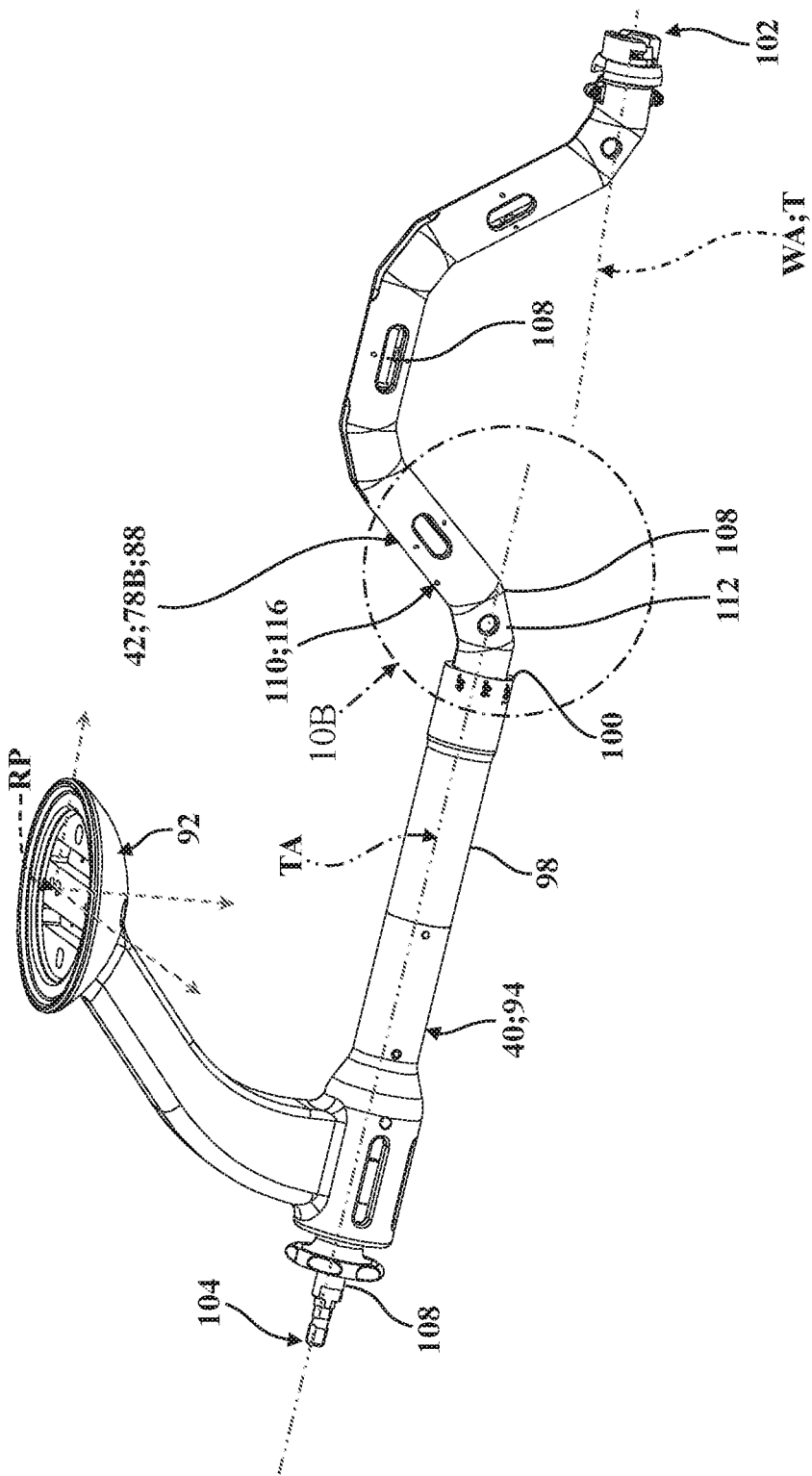
FIG. 10A is a perspective view of an end effector with a tool realized as a first-option reamer for use with the surgical system of FIG. 1.

The working end 102 of each tool 42 defines a respective workpiece axis WA, which may be coincident with the tool axis TA for some tools 42 (e.g., the straight impactor 80 depicted in FIG. 5A), parallel to and offset from the tool axis TA for some tools 42 (e.g., the second-option reamer 90 depicted in FIGS. 11A, 12A, and 13A), or angled with respect to the tool axis TA (e.g., the first-option reamer 88 depicted in FIG. 10A). Generally, the workpiece axis WA is coincident with the trajectory T maintained by the surgical robot 32.

The working ends 102 of the tools 42 each generally rotate and translate concurrently with their respective tool bodies 108. For the impactors 80, 82, 84, a head (not shown) may be coupled to the proximal end 104 to receive external impact force, such as from a mallet (not shown) to translate the tool body 108 and the working end 102 relative to the guide 94 and thereby facilitate installing the prosthetic cup (not shown) at the surgical site ST. For the reamers 86, 88, 90, a rotary instrument (not shown) may be coupled to the proximal end 104 to rotate the tool body 108 and the working end 102 relative to the guide 94 and thereby facilitate reaming (not shown) or otherwise preparing the surgical site ST for impaction. The tool bodies 108 of the reamers 86, 88, 90 also comprise handles, generally indicated at 112, and may include one or more universal joints, generally indicated at 114 where the tool axis TA is not coincident with the workpiece axis WA (see FIGS. 10A, 11A, 12A, and 13A). The handles 112 may be grasped by the surgeon and do not rotate concurrently with the working end 102 in response to rotational torque applied to the proximal end 104. The checkpoint features 110 of the reamers 86, 88, 90 are formed in the handles 112 of the tool bodies 108, as described in greater detail below. The universal joints 114 are employed in the first-option reamer 88 and the second-option reamer 90 to allow the tool body 108, which may be comprised of discrete sections (not shown in detail) to rotate between the proximal end 104 and the working end 102.

Referring again to FIGS. 1-14, the tools 42 within each toolset 78A, 78B each comprise one or more checkpoint features 110 formed in the tool body 108 at respective predetermined locations relative to the common reference point RP, as noted above. In the representative embodiment illustrated herein, the reference point RP is established when the coupling 106 of the tool 42 is engaged with the receiver 96 of the guide 94, and the end effector 40 is attached to the coupler 38 of the surgical robot 32. While the reference point RP could be defined or otherwise established in a number of different ways, because each of the exemplary tools 42 described and illustrated herein can be releasably attached to the same end effector 40, the reference point RP depicted in the drawings is located adjacent to the mount 92 of the end effector 40. As will be appreciated from the subsequent description below, because the surgical system 30 is able to determine the specific position and orientation of the coupler 38 of the surgical robot 32 within either coordinate system MNPL, LCLZ (e.g., via encoder data ED from the robotic arm 36 and/or via location data from the localizer 60 about the end effector tracker 62E), the location of the reference point RP is similarly known by the surgical system 30 during use. The reference point RP may also be known in a tool coordinate system associated with the end effector tracker 62E, with the reference point RP being stored as a coordinate, plane, line, or the like in the tool coordinate system and capable of being tracked by virtue of tracking the end effector tracker 62E. The relationship of the reference point RP to the end effector tracker 62E can be established by calibration, such as during manufacture or intraoperatively, or may be measured.

The surgical system 30 is configured to differentiate between the tools 42 of one or more toolsets 78A, 78B based on the location of the checkpoint features 110 with respect to the reference point RP to, among other things, ensure proper operation of the robotic control system 52 and/or the navigation system 54 by correctly positioning the tool 42 and/or workpiece 44. Here, each tool 42 comprises one or more checkpoint features 110 arranged at predetermined locations which are unique to that particular tool 42 within its respective toolset 78A, 78B. In the representative embodiment illustrated herein, the checkpoint features 110 are realized as divots 116 formed in the respective tool bodies 108: the straight impactor 80 comprises two divots 116ISTA, 116ISTB (see FIG. 5B); the first-option impactor 82 comprises one divot 116IFO (see FIG. 6B); the second-option impactor 84 comprises two divots 116ISOA, 116ISOB (see FIG. 7B); the straight reamer 86 comprises two divots 116RSTA, 116RSTB (see FIG. 9B); the first-option reamer 88 comprises two divots 116RFOA, 116RFOB (see FIG. 10B); and the second-option reamer 90 comprises two divots 116RSO1, 116RSO2 (see FIGS. 11B, 12B, and 13B). The divots 116 each have a generally frustoconical profile which is shaped to receive the distal tip 50B of the pointer 50, as described in greater detail below. However, it will be appreciated that the checkpoint features 110 could be configured in other ways, with or without the use of divots 116, sufficient to differentiate between tools 42 relative to the reference point RP. For the purposes of clarity and consistency, the arrangement, orientation, and configuration of the divots 116 will be described for each toolset 78A, 78B separately.

Referring now to FIGS. 5A-8, the impactors 80, 82, 84 of the first toolset 78A are shown. The straight impactor 80 is depicted in FIGS. 5A-5B. As shown in FIG. 5B, the checkpoint feature 110 of the straight impactor 80 comprises two divots 116ISTA, 116ISTB which are each formed in the tool body 108 at respective predetermined locations relative to the reference point RP. Because the tool body 108 of the straight impactor 80 is arranged for rotation about the tool axis TA relative to the mount 92 of the end effector 40, as noted above, movement of the tool body 108 effects corresponding movement of the checkpoint feature 110 relative to the reference point RP within a predetermined checkpoint space 118. In the illustrated embodiment of the straight impactor 80, the checkpoint space 118I_ST is defined by a circle disposed about and concentrically aligned with the tool axis TA (see FIGS. 5B and 8). Thus, irrespective of how the straight impactor 80 is rotated about the tool axis TA, its divots 116ISTA, 116ISTB will be positioned somewhere along the circular checkpoint space 118I_ST.

The first-option impactor 82 is depicted in FIGS. 6A-6B. As shown in FIG. 6B, the checkpoint feature 110 of the first-option impactor 82 comprises one divot 116IFO which is formed in the tool body 108 at a predetermined location relative to the reference point RP. Here too, because the tool body 108 of the first-option impactor 82 is arranged for rotation about the tool axis TA relative to the mount 92 of the end effector 40, movement of the tool body 108 effects corresponding movement of the checkpoint feature 110 relative to the reference point RP within a predetermined checkpoint space 118I_FO defined by a circle disposed about and concentrically aligned with the tool axis TA (see FIGS. 6B and 8). Thus, irrespective of how the first-option impactor 82 is rotated about the tool axis TA, its divot 116IFO will be positioned somewhere along the circular checkpoint space 118I_FO.

The second-option impactor 84 is depicted in FIGS. 7A-7B. As shown in FIG. 7B, the checkpoint feature 110 of the second-option impactor 84 comprises two divots 116ISOA, 116ISOB which are each formed in the tool body 108 at respective predetermined locations relative to the reference point RP. Here too, because the tool body 108 of the second-option impactor 84 is arranged for rotation about the tool axis TA relative to the mount 92 of the end effector 40, movement of the tool body 108 effects corresponding movement of the checkpoint feature 110 relative to the reference point RP within a predetermined checkpoint space 118I_SO defined by a circle disposed about and concentrically aligned with the tool axis TA (see FIGS. 7B and 8). Thus, irrespective of how the second-option impactor 80 is rotated about the tool axis TA, its divots 116ISOA, 116ISOB will be positioned somewhere along the circular checkpoint space 118I_SO.

Figure 8:
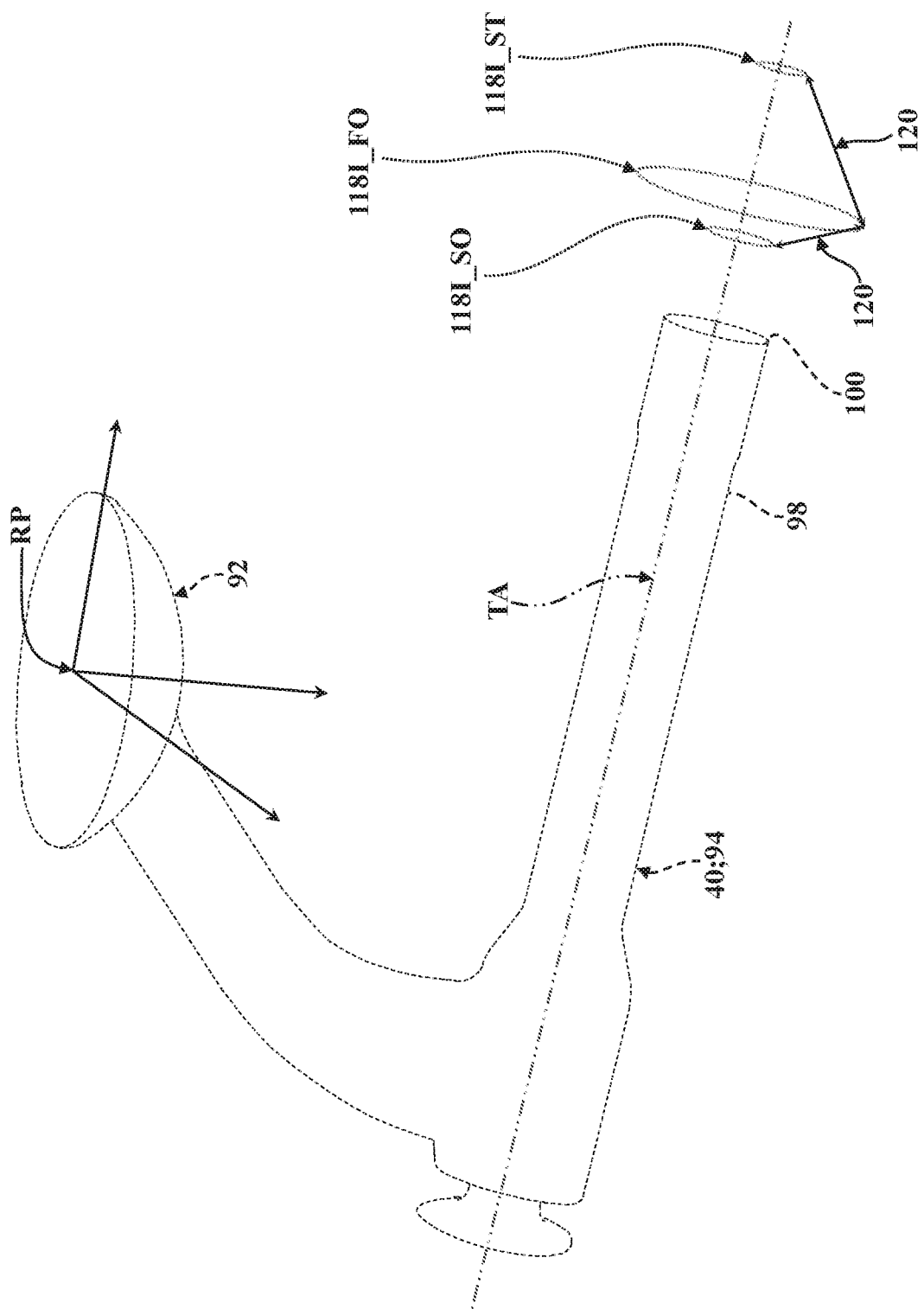
FIG. 8 is a perspective view of an end effector depicted in phantom, shown with the circular checkpoint spaces of FIGS. 5B, 6B, and 7B spaced from each other and from a reference point.

In FIG. 8, the checkpoint space 118I_ST of the straight impactor 80, the checkpoint space 118I_FO of the first-option impactor 82, and the checkpoint space 118I_SO of the second-option impactor 84 are each shown at their respective predetermined locations relative to the reference point RP established or otherwise defined by the end effector 40, as noted above. Each of the checkpoint spaces 118I_ST, 118I_FO, 118I_SO shown in FIG. 8 are spaced from each other such that a predetermined distance 120 (or more) separates adjacent checkpoint spaces 118I_ST, 118I_FO, 118I_SO from each other. Put differently, the predetermined location of the checkpoint feature 110 of each of the impactors 80, 82, 84 are arranged so as to be spaced from the checkpoint features 110 of each of the other impactors 80, 82, 84 at a minimum of the predetermined distance 120.

Here, because the impactors 80, 82, 84 are each arranged for rotation about the tool axis TA, it will be appreciated that the predetermined distance 120 extends in 3D space between any point along two adjacent checkpoint spaces 118I_ST, 118I_FO, 118I_SO (see FIG. 8). In one embodiment, the predetermined distance 120 is at least 10 mm.

Figure 9A:
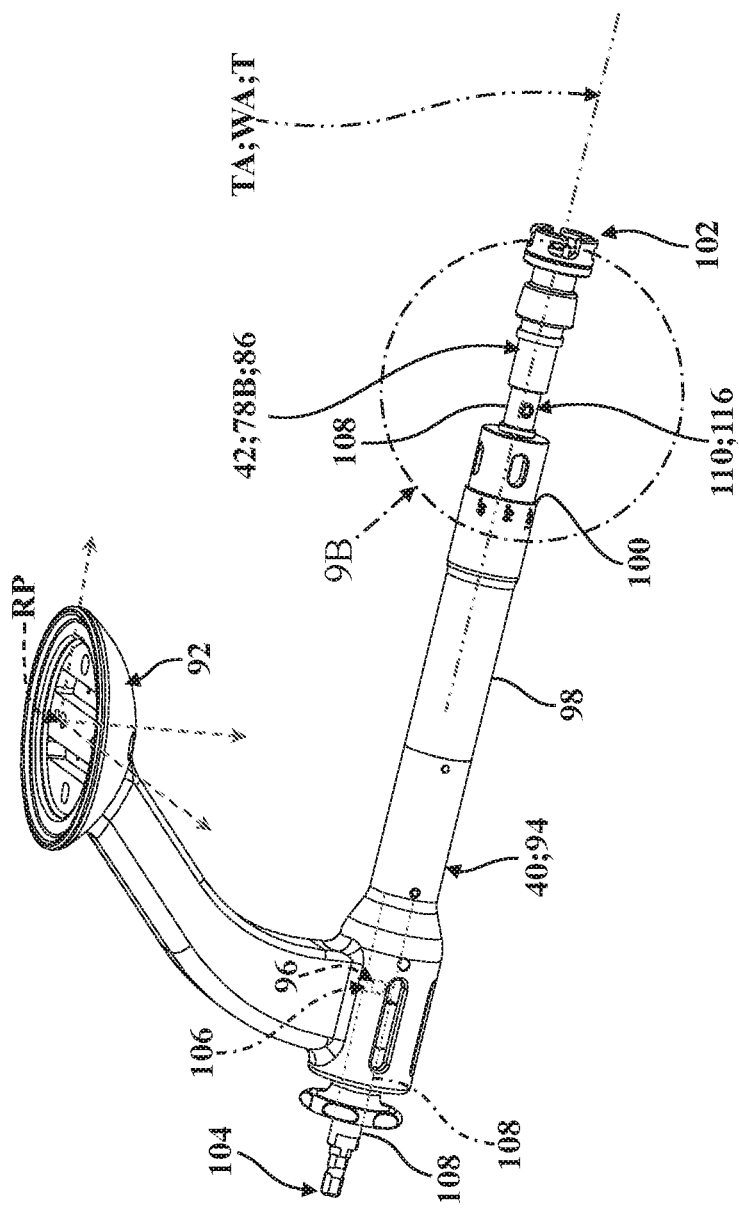
FIG. 9A is a perspective view of an end effector with a tool realized as a straight reamer for use with the surgical system of FIG. 1.
Figure 9B:
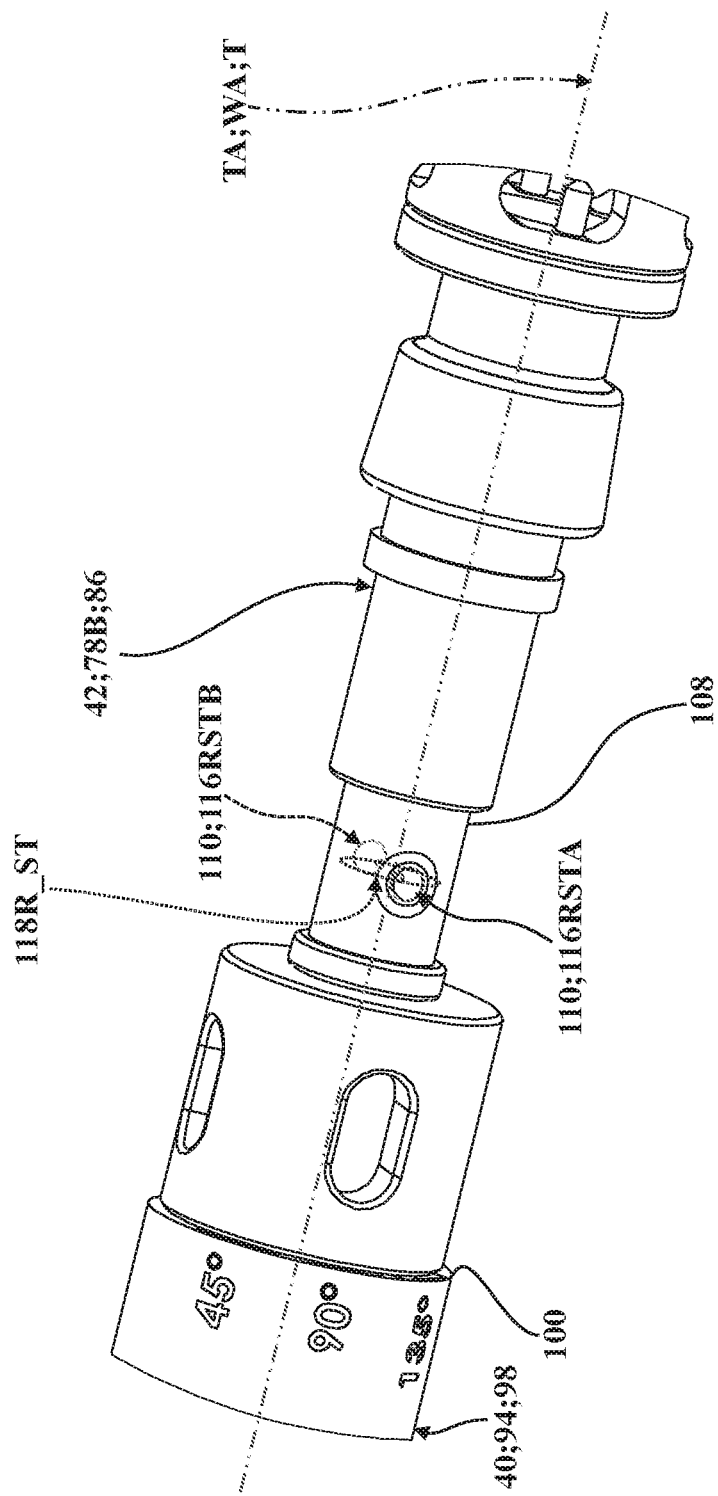
FIG. 9B is a partial, enlarged perspective view taken about indicia 9B in FIG. 9A, showing checkpoint features realized as divots (one divot shown in phantom) arranged about a circular checkpoint space.

Referring now to FIGS. 9A-14, the reamers 86, 88, 90 of the second toolset 78B are shown. The straight reamer 86 is depicted in FIGS. 9A-9B. As shown in FIG. 9B, the checkpoint feature 110 of the straight reamer 86 comprises two divots 116RSTA, 116RSTB which are each formed in the tool body 108 at respective predetermined locations relative to the reference point RP. Because the tool body 108 of the straight reamer 86 is arranged for rotation about the tool axis TA relative to the mount 92 of the end effector 40, as noted above, movement of the tool body 108 effects corresponding movement of the checkpoint feature 110 relative to the reference point RP within a predetermined checkpoint space 118. In the illustrated embodiment of the straight reamer 86, the checkpoint space 118R_ST is defined by a circle disposed about and concentrically aligned with the tool axis TA (see FIGS. 9B and 14). Thus, irrespective of how the straight reamer 86 is rotated about the tool axis TA, its divots 116RSTA, 116RSTB will be positioned somewhere along the circular checkpoint space 118R_ST.

Figure 10B:
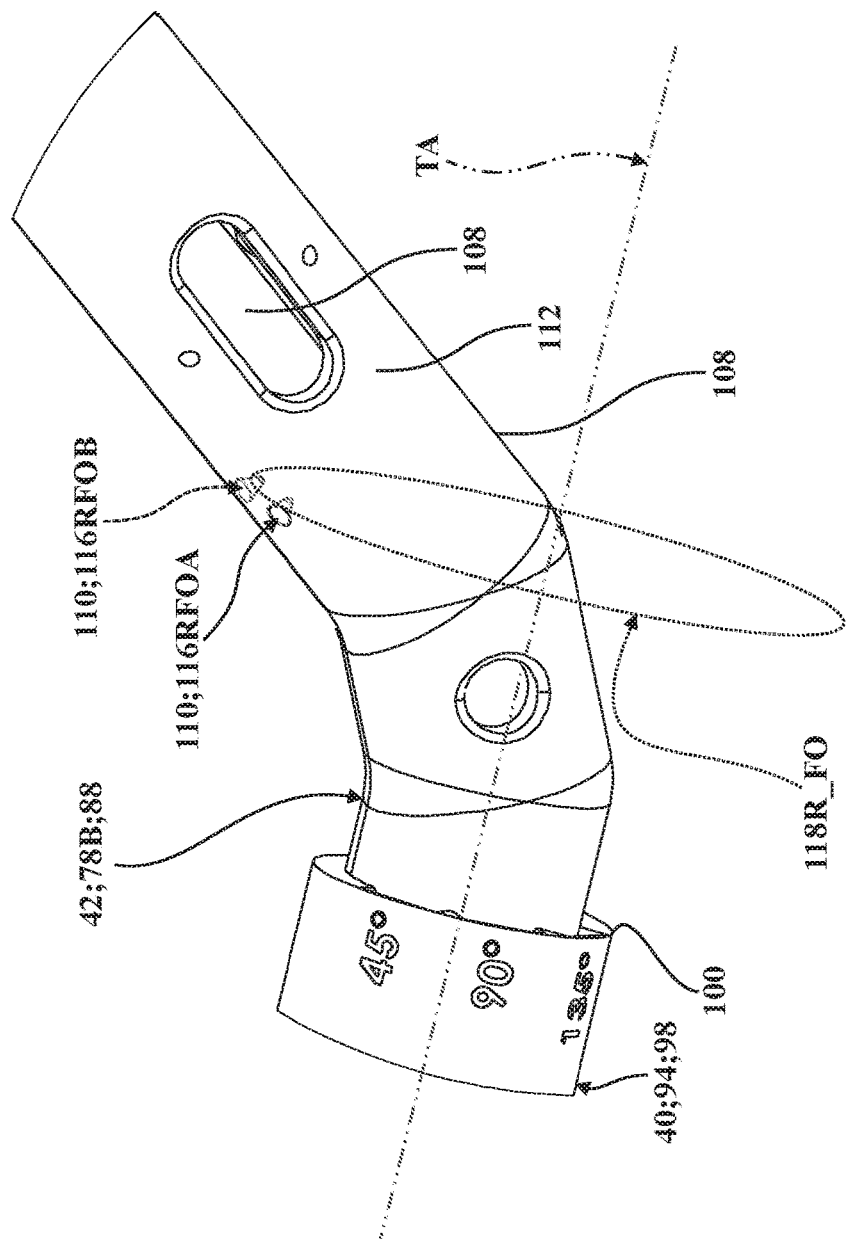
FIG. 10B is a partial, enlarged perspective view taken about indicia 10B in FIG. 10A, showing checkpoint features realized as divots (one divot shown in phantom) arranged about a circular checkpoint space.
Figure 11A:
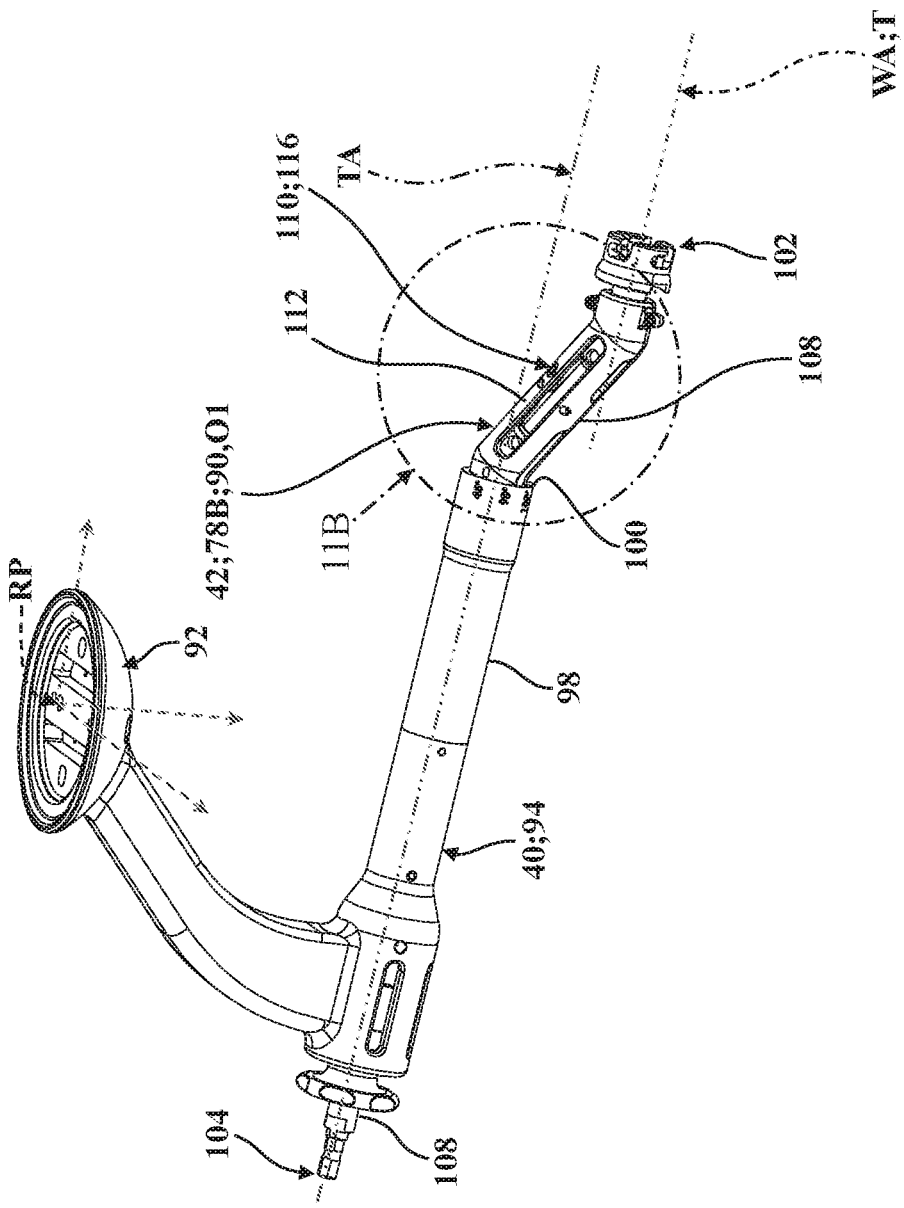
FIG. 11A is a perspective view of an end effector with a tool realized as a second-option reamer for use with the surgical system of FIG. 1, the second-option reamer shown arranged in a first orientation.
Figure 11B:
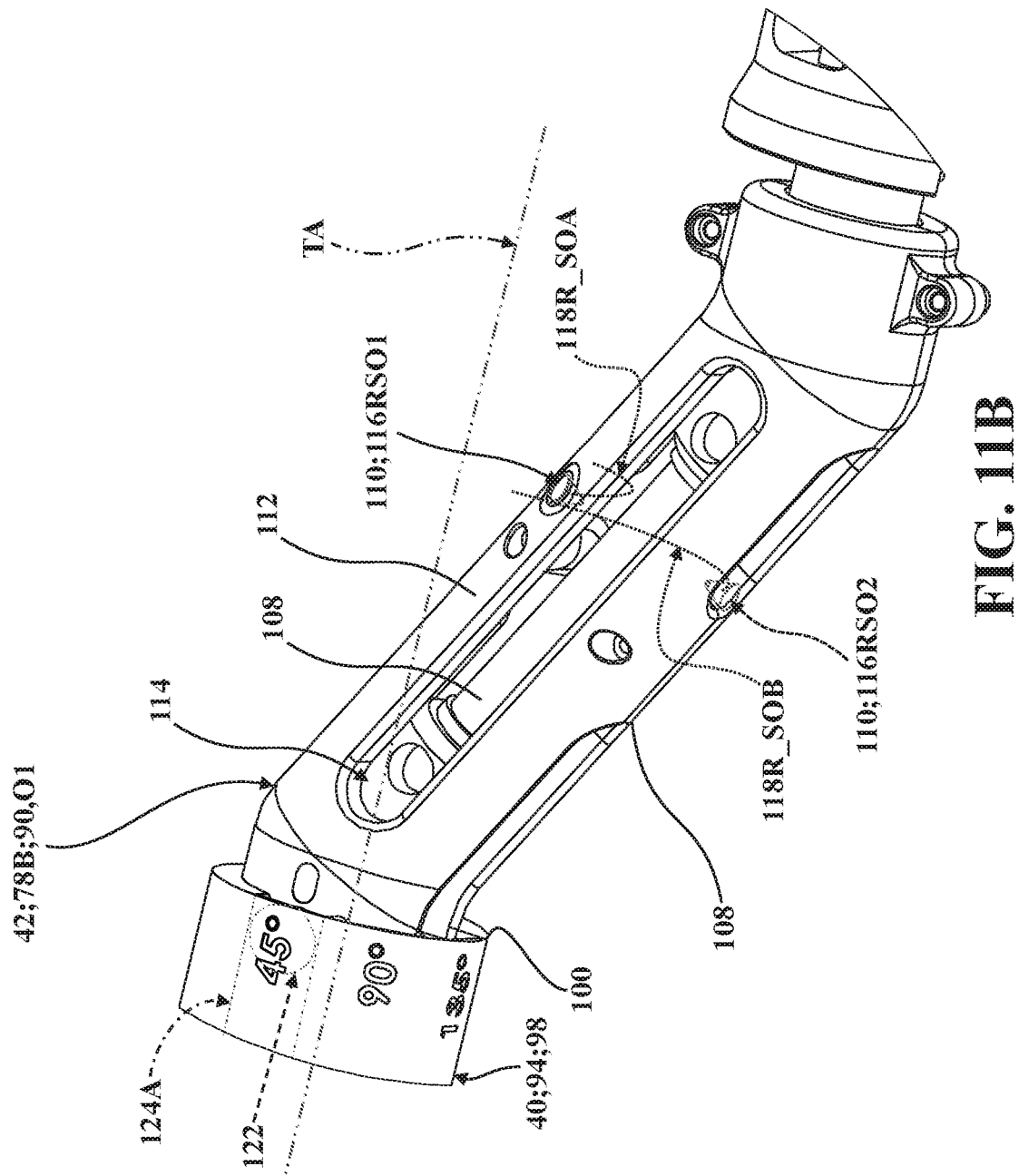
FIG. 11B is a partial, enlarged perspective view taken about indicia 11B in FIG. 11A, showing checkpoint features realized as divots (one divot shown in phantom) arranged along respective radial arc checkpoint spaces.
Figure 12A:
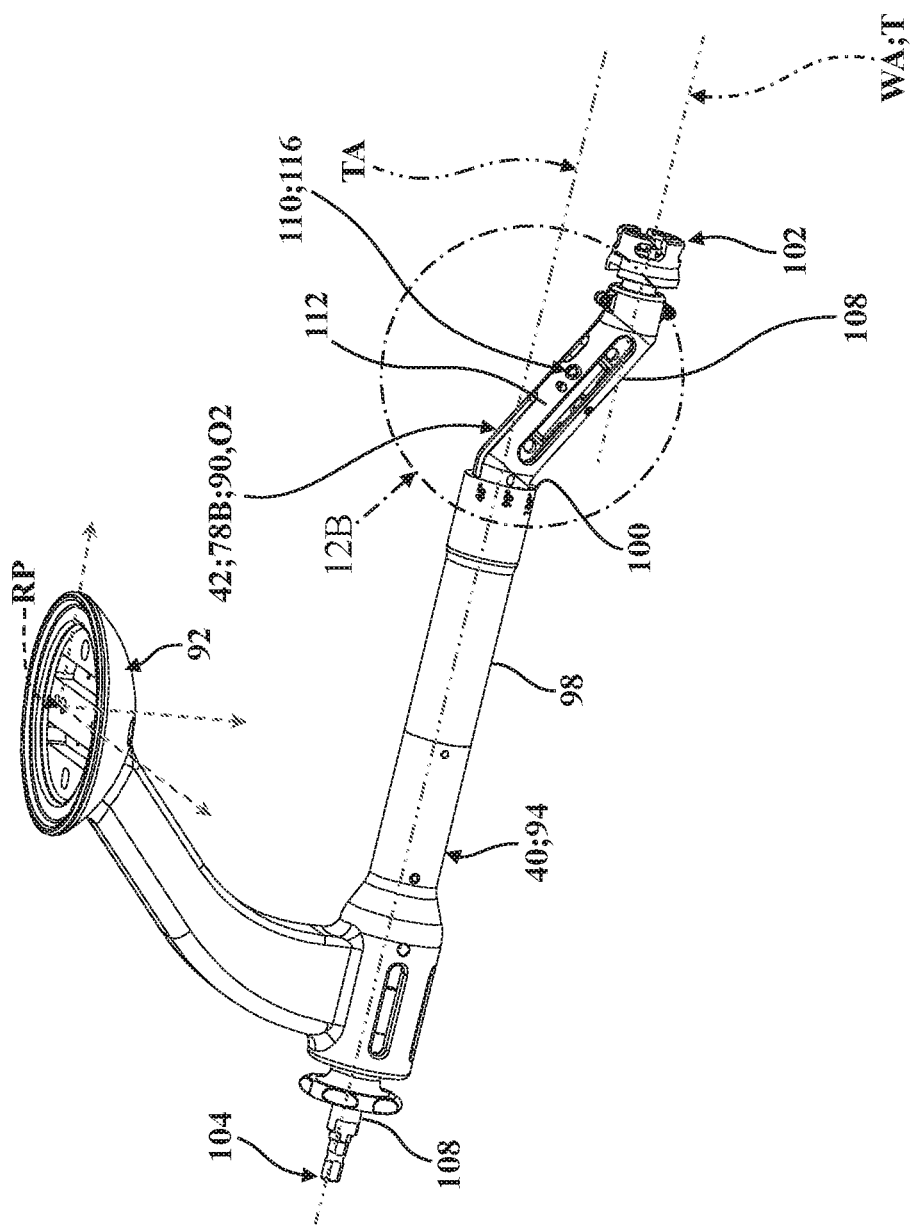
FIG. 12A is another perspective view of the end effector and second-option reamer of FIGS. 11A-11B, shown arranged in a second orientation.

The first-option reamer 88 is depicted in FIGS. 10A-10B. As shown in FIG. 10B, the checkpoint feature 110 of the first-option reamer 88 comprises two divots 116RFOA, 116RFOB which are formed in the tool body 108 at respective predetermined locations relative to the reference point RP. Here too, because the tool body 108 of the first-option reamer 88 is arranged for rotation about the tool axis TA relative to the mount 92 of the end effector 40, movement of the tool body 108 effects corresponding movement of the checkpoint feature 110 relative to the reference point RP within a predetermined checkpoint space 118R_FO defined by a circle disposed about and concentrically aligned with the tool axis TA (see FIGS. 10B and 14). Thus, irrespective of how the first-option reamer 88 is rotated about the tool axis TA, its divots 116RFOA, 116RFOB will be positioned somewhere along the circular checkpoint space 118R_FO.

Figure 13A:
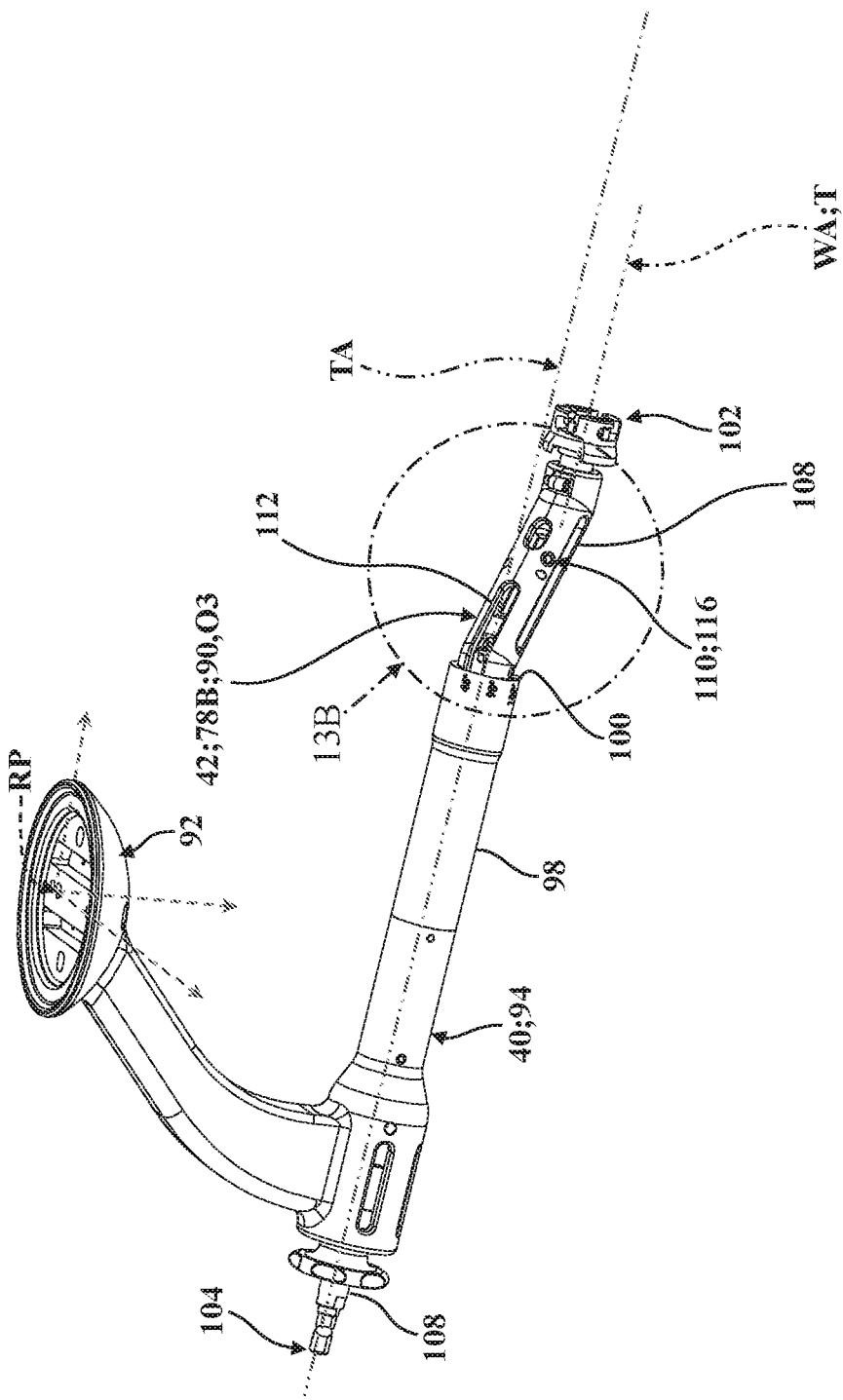
FIG. 13A is another perspective view of the end effector and second-option reamer of FIGS. 11A-12B, shown arranged in a third orientation.
Figure 13B:
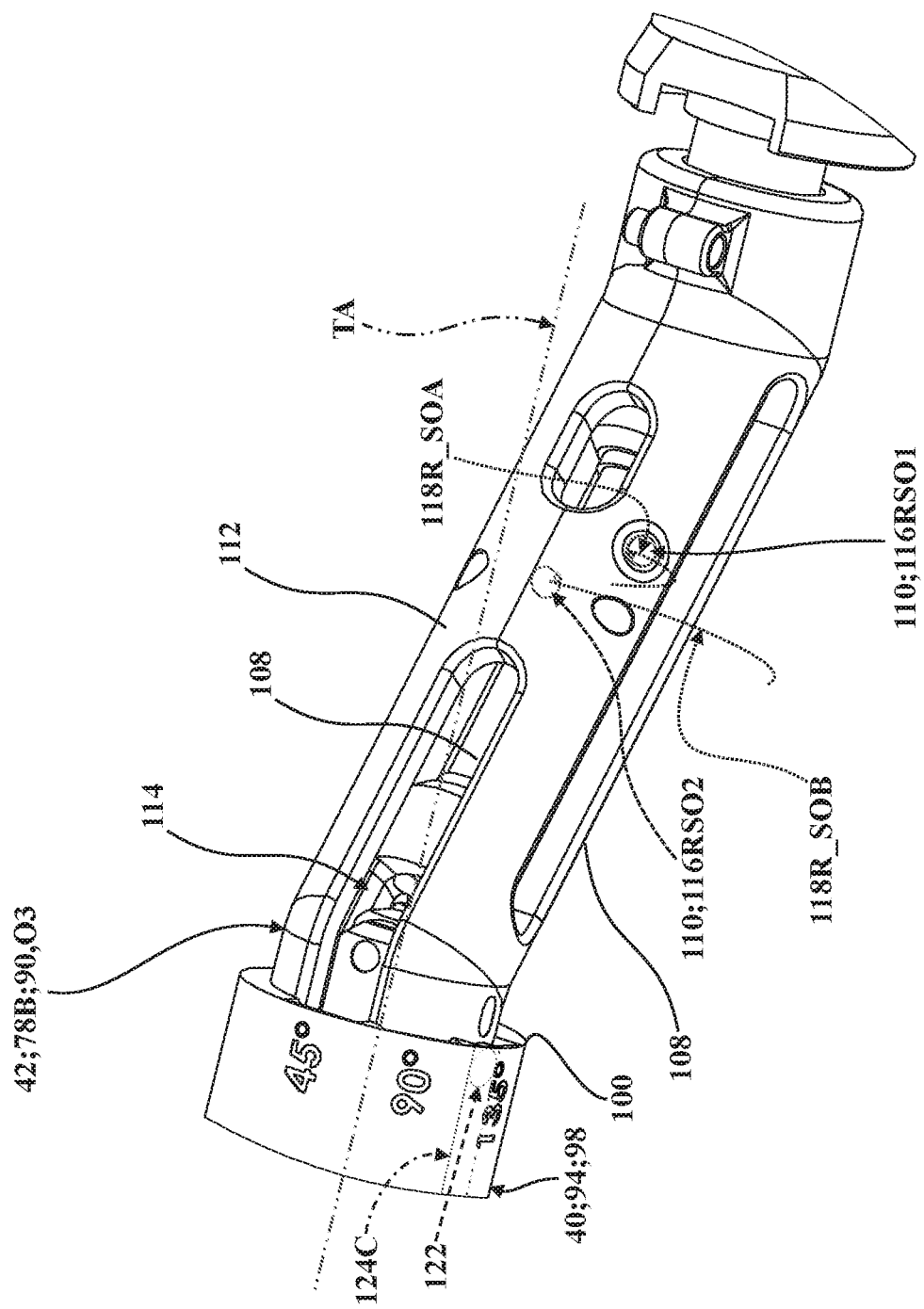
FIG. 13B is a partial, enlarged perspective view taken about indicia 13B in FIG. 13A, showing the checkpoint features realized as divots (one divot shown in phantom) arranged along respective radial arc checkpoint spaces.

The second-option reamer 90 is depicted in FIGS. 11A-13B. As shown in FIGS. 11B, 12B, and 13B, the checkpoint feature 110 of the second-option reamer 90 comprises two divots 116RSO1, 116RSO2 which are each formed in the tool body 108 at respective predetermined locations relative to the reference point RP. As noted above, the second-option reamer 90 does not freely rotate about the tool axis TA relative to the mount 92 of the end effector 40. Rather, in this embodiment, as is depicted schematically in FIGS. 11B, 12B, and 13B, the handle 112 of the second-option reamer 90 comprises a key 122 which can be received in either a first, second, or third keyways 124A, 124B, 124C formed in the cylindrical region 98 of the guide 94 adjacent to the distal guide end 100. Thus, the surgeon can position the key 122 in the first keyway 124A to place the second-option reamer 90 in the first orientation O1 (see FIGS. 11A-11B), in the second keyway 124B to place the second-option reamer 90 in the second orientation O2 (see FIGS. 12A-12B), or in the third keyway 124C to place the second-option reamer 90 in the third orientation O3 (see FIGS. 13A-13B). Furthermore, the illustrated embodiment of the second-option reamer 90 comprises different checkpoint features 110 respectively defined by the divots 116RSO1, 116RSO2. Here, movement between the first, second, and third orientations O1, O2, O3 effects corresponding movement of the checkpoint features 110 relative to the reference point RP within respective predetermined checkpoint spaces 118R_SOA, 118R_SOB each defined by a radial arc disposed about and concentrically aligned with the tool axis TA (see FIGS. 11B, 12B, 13B, and 14). Thus, irrespective of which orientation O1, O2, O3 the second-option impactor 80 is placed in, its divots 116RSO1, 116RSO2 will be positioned somewhere along the respective radial arc checkpoint spaces 118R_SOA, 118R_SOB. Furthermore, while the checkpoint features 110 of the illustrated embodiment of the second-option impactor 80 are configured such that the checkpoint spaces 118R_SOA, 118R_SOB are also spaced from each other at the predetermined distance 120, it is conceivable that the checkpoint spaces 118R_SOA, 118R_SOB could be arranged differently in some embodiments.

Figure 14:
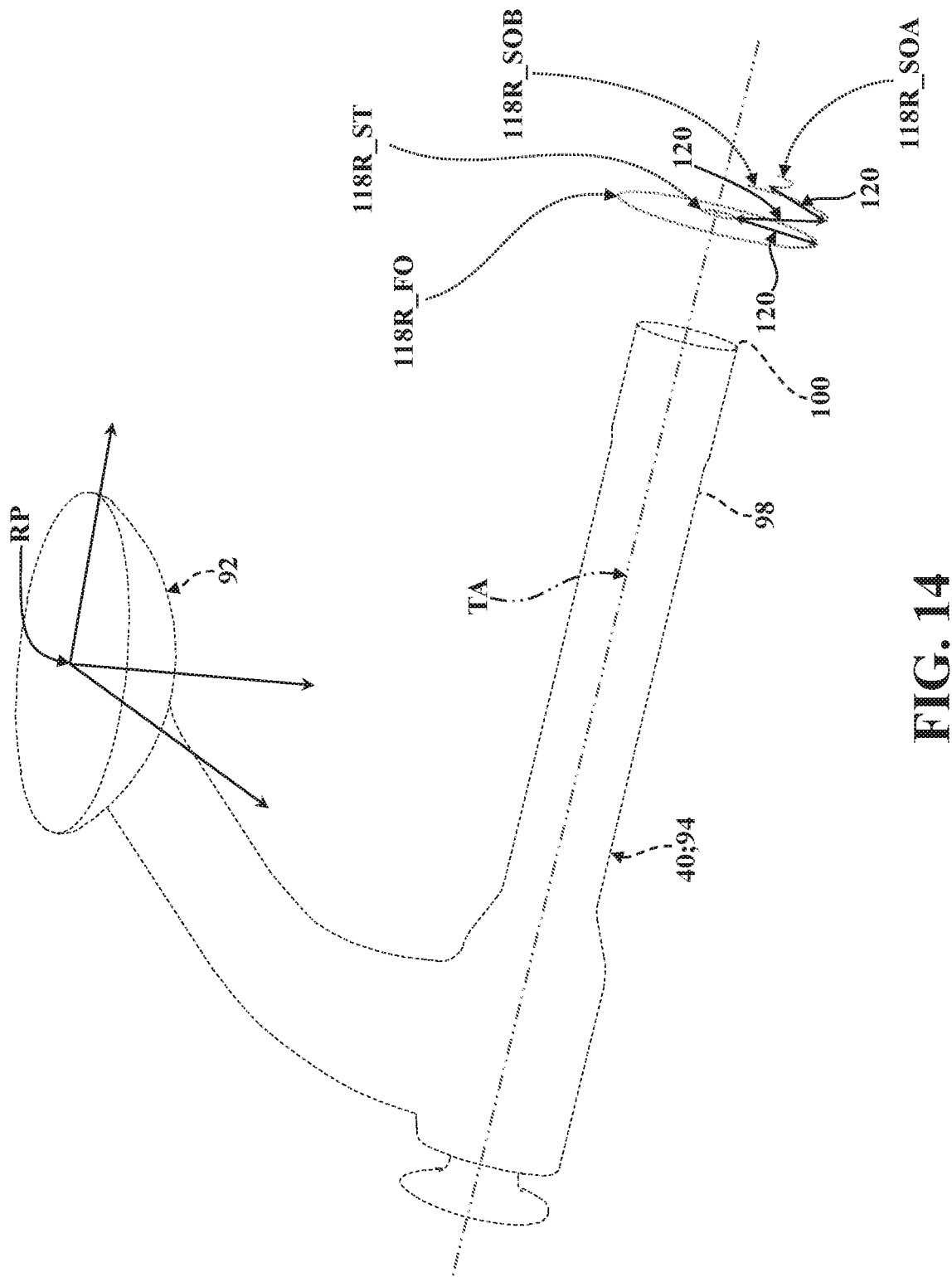
FIG. 14 is a perspective view of an end effector depicted in phantom, shown with the circular checkpoint spaces of FIGS. 9B and 10B and the radial arc checkpoint spaces of FIGS. 11B, 12B, and 13B spaced from each other and from a reference point.

In FIG. 14, the checkpoint space 118R_ST of the straight reamer 86, the checkpoint space 118R_FO of the first-option reamer 88, and the checkpoint spaces 118R_SOA, 118R_SOB of the second-option reamer 90 are each shown at their respective predetermined locations relative to the reference point RP established or otherwise defined by the end effector 40, as noted above. Each of the checkpoint spaces 118R_ST, 118R_FO, 118R_SOA, 118R_SOB shown in FIG. 14 are similarly spaced from each other such that the predetermined distance 120 (or more) separates adjacent checkpoint spaces 118R_ST; 118R_FO; 118R_SOA, 118R_SOB from each other. Put differently, the predetermined location of the checkpoint features 110 of each of the reamers 86, 88, 90 are arranged so as to be spaced from the checkpoint features 110 of each of the other reamers 86, 88, 90 at a minimum of the predetermined distance 120. Here, because the reamers 86, 88, 90 are each arranged for some form of movement about the tool axis TA (either free rotation or movement between discrete positions), it will be appreciated that the predetermined distance 120 similarly extends in 3D space between any point along two adjacent checkpoint spaces 118R_ST; 118R_FO; 118R_SOA, 118R_SOB (see FIG. 14).

While some of the tools 42 described above are able to freely rotate about the tool axis TA such that their checkpoint feature 110 could be disposed in a number of different predetermined locations about its respective circular checkpoint space 118, it will be appreciated that other configurations are contemplated. By way of non-limiting example, while the handle 112 of the second-option reamer 90 does not freely rotate about the tool axis TA and can be moved between the three orientations O1, O2, O3, it is conceivable that only a single orientation could be utilized in some embodiments such that the checkpoint feature 110 is defined by a point in space as opposed to a point along a circle or a radial arc. Furthermore, while some of the tools 42 described above employ checkpoint features 110 defined by multiple divots 116 that can occupy a common checkpoint space 118, only a single divot 116 could be employed in some embodiments. Moreover, multiple checkpoint features 110 with one or more divots 116 that occupy respective checkpoint spaces 118 could also be employed. Other configurations are contemplated.

Referring again to FIGS. 1-14, as noted above, the surgical system 30 is configured to differentiate between the tools 42 of one or more toolsets 78A, 78B based on the location of the checkpoint features 110 with respect to the reference point RP via the controller 46. Here, the controller 46 is configured to identify the tool 42 that is attached to the coupler 38 of the end effector 40 by monitoring the position and orientation of the pointer tracker 62P of the pointer 50 via the localizer 60 under certain operating conditions.

The controller 46 is configured to send different interface images IM (see FIGS. 3A-4C) stored in the memory 48 to the monitor 68M to assist the surgeon (or another user) in performing the surgical procedure. The interface images IM may be static images or may be defined as a part of a dynamic, navigable graphical user interface. In one embodiment, the controller 46 is configured to send a first interface image IM1 (see FIGS. 3A and 4A) to the monitor 68M prompting the surgeon (or another user) to position the distal tip 50D of the pointer 50 at the checkpoint feature 110 of the tool 42 attached to the coupler 38 of the surgical robot 32. Here, the controller 46 is further configured to receive position data PD (see FIG. 2) from the localizer 60 associated with the pointer tracker 62P of the pointer 50 within the field of view FV, and use this position data PD in order to compare the current position of the checkpoint feature 110 against the identification data ID stored in the memory 48 to determine the identity of (or "recognize") the tool 42.

In some embodiments, the coordinates of the distal tip 50D of the pointer 50 relative to its pointer tracker 62P is calibrated or known to the localizer 60 or the navigation controller 58 via calibration data stored in memory and accessible by the localizer 60 and/or the navigation controller 58. As a result, the localizer 60 and/or the navigation controller 58 are able to determine coordinates of the distal tip 50D of the pointer 50 in the localizer coordinate system LCLZ, the manipulator coordinate system MNPL, the tool coordinate system (via transformation techniques described above), or in some other common coordinate system. Current coordinates of the reference point RP can similarly be determined using position data PD associated with the end effector tracker 62E. For example, coordinates of the reference point RP relative to the end effector tracker 62E can be calibrated or known to the localizer 60 or the navigation controller 58 via calibration data stored in memory and accessible by the localizer 60 and/or the navigation controller 58. Thus, by knowing the current coordinates of the reference point RP and the current coordinates of the checkpoint feature 110 in the common coordinate system, the localizer 60 and/or the navigation controller 58 can compare the relationship (e.g., positional relationship between coordinates) of the reference point and the checkpoint feature 110 and compare this relationship to stored, expected relationships for each of the different tools 42, e.g., the identification data ID.

In some embodiments, the identification data ID associated with the tools 42 and stored in the memory 48 comprise coordinates of the predetermined locations associated with the checkpoint features 110 of each tool 42 within the respective toolset 78A, 78B. More specifically, the identification data ID may comprise coordinates and/or areas disposed along the checkpoint spaces 118 of each tool 42 within the respective toolset 78A, 78B, and relative to the reference point RP. In some cases, these coordinates and/or areas, along with the coordinates of the reference point RP, can be stored in the tool coordinate system to establish a known relationship between the reference point RP and the checkpoints 110 and/or checkpoint spaces 118. Thus, the actual coordinates of the checkpoint 110 determined by the pointer 50 can be determined in the tool coordinate system (e.g., via transformation techniques described above), compared to the stored, possible coordinates of the checkpoint 110 in the tool coordinate system, with the best fit selected to thereby identify the correct tool 42. If no match is found because the measured coordinates differ beyond a predetermined threshold from each of the stored coordinates, then the surgeon may be prompted with instructions on the monitor 68M to recalibrate the pointer 50 or to ensure that the tool 42 is fully seated in the receiver 96.

Once the controller 46 has determined the identity of the tool 42, it sends a second interface image IM2 (see FIGS. 3B and 4B) to the monitor 68M to present the surgeon (or another user) with the identity of the tool 42. In some embodiments, the controller 46 is further configured to send a third interface image IM3 (see FIGS. 3C and 4C) to the monitor 68M to present the surgeon (or another user) with the identity of the tool 42 alongside a predetermined number of identities associated with the other tools 42 in the respective toolset 78A, 78B based on the identification data ID stored in the memory 48. In the embodiment illustrated in FIGS. 3A-4C, the second interface image IM2 (see FIGS. 3B and 4B) presents the identity of the tool 42 as a selection of a "drop down" list of identities (see FIGS. 3C and 4C). It will be appreciated that this configuration affords advantages in situations where the localizer 60 operates with less than optimal accuracy, such as where the field of view FV is narrow or obscured, where user error places the distal tip 50D of the pointer 50 out of alignment with the pointer tracker 62P, and the like. In such situations, the surgical system 30 could still be configured to present the surgeon (or another user) with the assumed identity of the tool 42 while, at the same time, requesting the surgeon to manually verify the identity of the tool 42 and notifying the surgeon to check for misalignment or to use a different pointer 50. Other configurations are contemplated.

It should be appreciated that the controller 46 may be configured to receive position data PD from the localizer 60 associated with the tool 42 within the field of view FV by tracking a base tracker (not shown) attached to the robotic arm 36, such as by monitoring the position and/or orientation of the base tracker, with the base tracker being registered to the manipulator coordinate system MNPL, and with encoder data ED being additionally used to determine a position of the reference point RP in the manipulator coordinate system MNPL. Similarly, the controller 46 can then compare the current position of the checkpoint 110 in the manipulator coordinate system MNPL relative to the current position of the reference point RP to the stored, possible positions of the checkpoint 110 based on its stored relationship to the reference point RP, e.g., against the identification data ID stored in the memory 48, to determine the identity of the tool 42. In some embodiments, position data PD associated with the tool 42 may be at least partially determined using encoder data ED from the robot controller 56.

The present disclosure is also directed toward a method of assisting the surgeon (or another user) in performing the surgical procedure with the surgical system 30. The method comprises different steps, including attaching the tool 42 having the checkpoint feature 110 to the surgical robot 32, and sending the first interface image IM1 to the monitor 68M prompting the surgeon to position the distal tip 50D of the pointer 50 at the checkpoint feature 110 of the tool 42. The method also comprises tracking the pointer 50 with the localizer 60 to determine position data PD associated with the pointer 50, identifying the tool 42 by comparing the position data PD from the localizer 60 with stored identification data ID, and sending a second interface image IM2 to the monitor 68M presenting the surgeon with the identity of the tool 42.

The embodiments of the surgical system 30, end effector 40, tools 42, and methods described herein afford advantages in connection with a broad number of medical and/or surgical procedures including, for example, where surgical robots 32 are utilized in connection with total hip arthroplasty. Specifically, it will be appreciated that the embodiments described and illustrated herein are configured to facilitate identification of different variations of tools 42 in one or more toolsets 78A, 78B quickly, reliably, and efficiently while, at the same time, affording the surgeon with guided assistance in carrying out different types of surgical procedures.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A surgical system for assisting a user in performing a surgical procedure at a surgical site, said surgical system comprising:
   a tool having a checkpoint feature;
   a pointer having a distal tip;
   a localizer to determine a position of said pointer within a field of view;
   a display;
   a memory comprising identification data associated with a plurality of tools; and
   a controller configured to prompt the user to position said distal tip of said pointer at said checkpoint feature of said tool, to receive position data from said localizer associated with said pointer within said field of view, to compare position data associated with said pointer against said identification data of said memory to determine an identity of said tool, and to present the user with said identity of said tool alongside a predetermined number of identities associated with other tools based on said identification data of said memory on said display.

2. The surgical system as set forth in claim 1, wherein said localizer is further configured to determine a position of said tool within said field of view.

3. The surgical system as set forth in claim 2, wherein said controller is further configured to receive position data from said localizer associated with said tool within said field of view, and to compare position data associated with said pointer and position data associated with said tool against said identification data of said memory to determine said identity of said tool.

4. The surgical system as set forth in claim 1, wherein said tool comprises a first end effector adapted for attachment to a surgical robot to establish a reference point for said tool; and
   wherein said checkpoint feature is further defined as a first checkpoint feature arranged at a first predetermined location defined with respect to the reference point.

5. The surgical system as set forth in claim 4, further comprising a second end effector adapted for attachment to the surgical robot to establish the reference point for said second end effector, said second end effector having a second checkpoint feature arranged at a second predetermined location, different from said first predetermined location, defined with respect to the reference point.

6. The surgical system as set forth in claim 5, wherein said identification data of said memory comprise coordinates of said first and second checkpoint features at said first and second predetermined locations with respect to the reference point.

7. The surgical system as set forth in claim 5, wherein said first predetermined location and said second predetermined location are spaced from each other at a predetermined distance.

8. The surgical system as set forth in claim 7, wherein said predetermined distance is at least 10 mm.

9. The surgical system as set forth in claim 1, wherein said tool comprises an end effector having a mount adapted for attachment to a surgical robot to establish a reference point for said tool, and having a tool body coupled to said mount with said checkpoint feature formed in said tool body arranged at a predetermined location defined with respect to the reference point.

10. The surgical system as set forth in claim 9, wherein said tool body of said end effector comprises a working end to support a workpiece at the surgical site along a trajectory maintained by the surgical robot.

11. The surgical system as set forth in claim 9, wherein said tool body is arranged for movement relative to said mount to effect corresponding movement of said checkpoint feature relative to the reference point within a predetermined checkpoint space.

12. The surgical system as set forth in claim 11, wherein said identification data of said memory represent coordinates disposed along said predetermined checkpoint space.

13. The surgical system as set forth in claim 11, wherein said checkpoint feature comprises a divot formed in said tool body and disposed within said checkpoint space.

14. The surgical system as set forth in claim 11, wherein said checkpoint feature comprises a plurality of divots formed in said tool body with each of said plurality of divots disposed within said checkpoint space.

15. The surgical system as set forth in claim 11, wherein said tool has a different checkpoint feature formed in said tool body arranged at a different predetermined location defined with respect to the reference point such that movement of said tool body relative to said mount effects corresponding movement of said different checkpoint feature relative to the reference point within a predetermined different checkpoint space.

16. The surgical system as set forth in claim 15, wherein said checkpoint feature comprises a divot formed in said tool body and disposed within said checkpoint space; and
   wherein said different checkpoint feature comprises a different divot formed in said tool body and disposed within said different checkpoint space.

17. The surgical system as set forth in claim 15, wherein said predetermined location and said different predetermined location are spaced from each other at a predetermined distance.

18. The surgical system as set forth in claim 11, wherein said checkpoint feature comprises a plurality of divots formed in said tool body with each of said plurality of divots disposed within said checkpoint space.

19. The surgical system as set forth in claim 11, wherein said tool body is arranged for rotational movement relative to said mount about a tool axis.

20. The surgical system as set forth in claim 19, wherein said checkpoint space is defined by a circle disposed about said tool axis.

21. The surgical system as set forth in claim 19, wherein said checkpoint space is defined by a radial arc disposed about said tool axis.

22. The surgical system as set forth in claim 1, wherein said checkpoint feature comprises a divot formed in said tool.

23. The surgical system as set forth in claim 1, wherein said memory further comprises interface images to assist the user in performing the surgical procedure;
wherein said display is configured to display said interface images; and
wherein said controller is further configured to send a first interface image to said display prompting the user to position said distal tip of said pointer at said checkpoint feature of said tool, to receive position data from said localizer associated with said pointer within said field of view, to compare position data associated with said pointer against said identification data of said memory to determine an identity of said tool, and to send a second interface image to said display presenting the user with said identity of said tool.

24. The surgical system as set forth in claim 23, wherein said controller is further configured to send a third interface image to said display presenting the user with said identity of said tool alongside said predetermined number of identities of said list of identities associated with other tools based on said identification data of said memory.

25. A toolset for driving a workpiece at a surgical site along a trajectory maintained by a surgical robot having a reference point, said toolset comprising:
a mount adapted to attach to the surgical robot;
a guide coupled to said mount and comprising a receiver;
a first tool having a first working end to support the workpiece, a first coupling to engage said receiver of said guide, and a first tool body extending between said first working end and said first coupling with a first checkpoint feature arranged at a first predetermined location that is spaced from the reference point by a first predetermined distance when said first coupling is engaged with said receiver and said mount is attached to the surgical robot; and
a second tool having a second working end to support the workpiece, a second coupling to engage said receiver of said guide, and a second tool body extending between said second working end and said second coupling with a second checkpoint feature arranged at a second predetermined location that is spaced from said reference point by a second predetermined distance that is different than said first predetermined distance when said second coupling is engaged with said receiver and said mount is attached to the surgical robot.

26. The toolset as set forth in claim 25, wherein the difference between said predetermined distances is at least 10 mm.

27. A method of assisting a user in performing a surgical procedure with a surgical system comprising a surgical robot, a localizer, and a display, said method comprising:
attaching a tool having a checkpoint feature to the surgical robot;
sending a first interface image to the display prompting the user to position a distal tip of the pointer at the checkpoint feature of the tool;
tracking the pointer with the localizer to determine position data associated with the pointer;
identifying the tool by comparing the position data from the localizer with stored identification data;
sending a second interface image to the display presenting the user with the identity of the tool alongside a predetermined number of identities associated with other tools based on the identification data of the memory.

* * * * *